United States Patent
Matsui et al.

(10) Patent No.: US 8,958,112 B2
(45) Date of Patent: Feb. 17, 2015

(54) DRUG MIXING PREPARATION MANAGING APPARATUS, CONTROL METHOD AND CONTROL PROGRAM

(71) Applicant: Toshiba Tec Kabushiki Kaisha, Tokyo (JP)

(72) Inventors: Shiomi Matsui, Shizuoka (JP); Yasutsugu Sasaki, Tokyo (JP); Maki Sato, Kanagawa (JP)

(73) Assignee: Toshiba Tec Kabushiki Kaisha, Tokyo (JP)

(*) Notice: Subject to any disclaimer, the term of this patent is extended or adjusted under 35 U.S.C. 154(b) by 0 days.

(21) Appl. No.: 13/943,539

(22) Filed: Jul. 16, 2013

(65) Prior Publication Data

US 2014/0022569 A1    Jan. 23, 2014

(30) Foreign Application Priority Data

Jul. 17, 2012  (JP) ................................ 2012-159072

(51) Int. Cl.
| | | |
|---|---|---|
| G06K 15/00 | (2006.01) | |
| G06F 15/00 | (2006.01) | |
| G06Q 10/00 | (2012.01) | |
| G06F 17/00 | (2006.01) | |
| G05B 21/00 | (2006.01) | |
| G06F 19/00 | (2011.01) | |

(52) U.S. Cl.
CPC ........ *G06F 19/3462* (2013.01); *G06F 19/3468* (2013.01)
USPC ............... 358/1.16; 358/1.9; 705/2; 700/231; 700/266

(58) Field of Classification Search
None
See application file for complete search history.

(56) References Cited

U.S. PATENT DOCUMENTS

| | | | | |
|---|---|---|---|---|
| 2008/0288287 | A1* | 11/2008 | Stanners ......................... | 705/2 |
| 2011/0060448 | A1* | 3/2011 | Gotou et al. .................. | 700/215 |
| 2013/0342676 | A1* | 12/2013 | Amano et al. .................. | 348/86 |

FOREIGN PATENT DOCUMENTS

| | | |
|---|---|---|
| JP | 2005046420 A | 2/2005 |
| JP | 2005-334056 | 12/2005 |
| JP | 2006-296912 | 11/2006 |
| WO | 2010113436 A1 | 10/2010 |

OTHER PUBLICATIONS

Japanese Office Action dated Jul. 15, 2014, filed in Japanese counterpart Application No. 2012-159072, 10 pages (with translation).

* cited by examiner

*Primary Examiner* — Thomas Lett
(74) *Attorney, Agent, or Firm* — Patterson & Sheridan, LLP

(57) ABSTRACT

A method of managing a mixed injection preparation process includes obtaining a mixed injection preparation instruction (e.g., a prescription) and obtaining information about a drug to be potentially included in the mixed injection according to the preparation instruction. The information about the candidate drug is compared to the preparation instruction and a determination as to whether the mixed injection is prepared in accordance with the mixed injection preparation instruction is made based on the information obtained about the candidate drug. A printer is used to print a label indicating whether the mixed injection is prepared in accordance with the mixed injection preparation instruction, and then it is determined whether the label is removed from the printer.

20 Claims, 33 Drawing Sheets

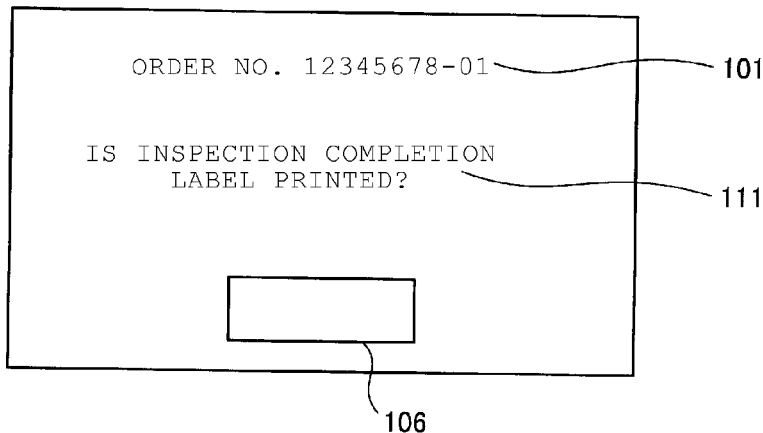

FIG. 18

| FIFTH FLOOR | DEPARTMENT OF INTERNAL MEDICINE | | DOSE OF JULY 18 | |
|---|---|---|---|---|
| FURIGANA (PHONETIC SUBSCRIPT) | ID: 12345678 | | | |
| ☐☐☐☐ ☐☐☐ | | | (CHEMICAL) | |
| BORN IN NOVEMBER 22, 1975 | 37 YEARS OLD | MALE | 12345678-01 | |
| Rp2 | | | | |
| INTRAVENOUS DRIP INJECTION TIP (1) | | | | |
| CCC INJECTION SOLUTION 10 mg | | | | |
| EXPIRATION OF EXPIRATION DATE | | | | RETURN |

FIG. 22

| FIFTH FLOOR | DEPARTMENT OF INTERNAL MEDICINE | | DOSE OF JULY 18 | |
|---|---|---|---|---|
| FURIGANA (PHONETIC SUBSCRIPT) | ID: 12345678 | | (CHEMICAL) | |
| ☐☐☐☐ ☐☐☐ | | | | |
| BORN IN NOVEMBER 22, 1975 | 37 YEARS OLD | MALE | 12345678-01 | |
| Rp2 | | | | |
| INTRAVENOUS DRIP INJECTION (ROUTINE NON-SELECTED) | | | | |
| CCC INJECTION SOLUTION 10 mg | | | | |
| EXCESSIVE AMOUNT | | | RETURN | |

FIG. 26

| FIFTH FLOOR | DEPARTMENT OF INTERNAL MEDICINE | | DOSE OF JULY 18 | |
|---|---|---|---|---|
| FURIGANA (PHONETIC SUBSCRIPT) | ID: 12345678 | | | |
| ☐☐☐☐ ☐☐☐ | | | | |
| BORN IN NOVEMBER 22, 1975 | 37 YEARS OLD | MALE | 12345678-01 | |
| Rp2 | | | | |
| INTRAVENOUS DRIP INJECTION (ROUTINE NON-SELECTED) | | | | |
| CCC INJECTION SOLUTION 10 mg | | | | |
| MISTAKEN DRUG PREPARATION | | | RETURN | |

139 — (left side labels)
137 — (top right)
101 — (right side)
138 — (barcode)
136 — CCC INJECTION SOLUTION 10 mg
135 — MISTAKEN DRUG PREPARATION

FIG. 30

| FIFTH FLOOR | DEPARTMENT OF INTERNAL MEDICINE | | DOSE OF JULY 18 | |
|---|---|---|---|---|
| FURIGANA (PHONETIC SUBSCRIPT) | ID: 12345678 | | (CHEMICAL) | |
| ☐☐☐☐ ☐☐☐ | | | | |
| BORN IN NOVEMBER 22, 1975 | 37 YEARS OLD | MALE | 0043075401 | |
| Rp3 | | | | |
| INTRAVENOUS DRIP INJECTION TIP (1) | | | | |
| AAA INTRAVENOUS INJECTION 1.5 g<br>BBB 500 mL | | | | |
| RE-SORTING | | | RETURN | |

141, 142, 143, 144, 145, 146, 147

DRUG MIXING PREPARATION MANAGING APPARATUS, CONTROL METHOD AND CONTROL PROGRAM

CROSS-REFERENCE TO RELATED APPLICATION

This application is based upon and claims the benefit of priority from Japanese Patent Application No. 2012-159072, filed Jul. 17, 2012, the entire contents of or all of which are incorporated herein by reference.

FIELD

Embodiments described herein relate generally to a drug mixing preparation managing apparatus, a control method, and a control program.

BACKGROUND

In a pharmacy of a hospital, a nurse's station of a hospital ward, or the like, a pharmacist or a nurse performs a drug mixing preparation (hereinafter, mixed injection preparation) of drugs prescribed on the basis of an instruction such as a prescription generated by a doctor or the like.

When a mixed injection preparation is performed, first, the pharmacist or the nurse sorts the drugs that to be included in the prescribed mixed injection preparation with reference to the instruction sheet. Likewise, the pharmacist or the nurse then performs measurement (of amounts such as weight or volume) of the drugs, dissolution, mixing, and the like, in an appropriate order with respect to the various components.

In order to ensure the mixed injection preparation is performed correctly, the pharmacist or nurse performs an inspection work whereby the pharmacist or nurse checks whether the drugs included in the mixed injection preparation are indeed the drugs prescribed by cross-referencing the labels of the drugs and the instruction sheet (injection prescription), before the mixed injection is prepared or administered.

However, there are several reasons why sorting and checking of drugs can be done erroneously or inappropriately and generate mistaken mixed injection preparations. Specifically, various human errors such as misreading of similar medicine names or failure to check or confirm an expiration date. So, even while pharmacists or nurses are generally careful in the inspection routine, occasional errors may still be made, and it is not easy to prevent erroneous mixed injection preparations.

Thus, several systems that support a preparation work to prevent or reduce the occurrence of preparation errors have been proposed. For example, a technique has been proposed in which a label to be attached to the mixed formulation obtained by mixed injection preparation is prepared in advance and the label is then attached to the new drug preparation after the mixed injection is completely formulated.

However, if the label is printed in advance, then the timing of when the label is attached to the drug is not clear, and thus, a problem may frequently occur that the attachment of the label is not made at an appropriate time or may be omitted.

DESCRIPTION OF THE DRAWINGS

FIG. 13 is a diagram illustrating an example of a label issue screen when all drugs are inspected and confirmed.

FIG. 14 is an example of a label issued when all drugs are inspected and confirmed.

FIG. 18 is an example of a label issued when an expiration date has passed.

FIG. 22 is an example of a label issued when the amount of a component is excessive.

FIG. 26 is an example of a label issued when a drug is mistakenly prepared.

FIG. 30 is an example of a label issued when re-sorting is performed.

DETAILED DESCRIPTION

Figure 1:
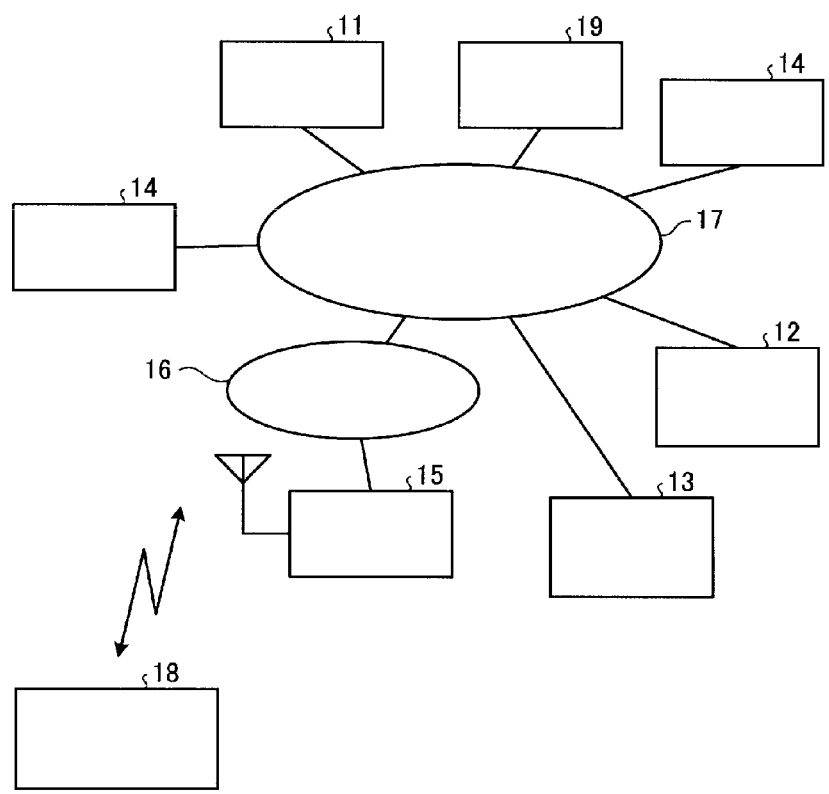
FIG. 1 is a block diagram of a schematic configuration of a drug mixing preparation managing system.

A method of managing a mixed injection preparation process, according to an embodiment, includes obtaining a mixed injection preparation instruction (e.g., a prescription) and obtaining information (e.g., drug name, dosage level, or expiration date) about a candidate drug for inclusion in the mixed injection. The information about the candidate drug is compared to the mixed injection preparation instruction, and then it is determined whether the mixed injection is correctly prepared according to the preparation instructions. After it is determined that the mixed injection is prepared according to the preparation instructions, a label indicating that the mixed injection has been prepared according to the instructions is printed with a printer. The method further includes determining whether the label is removed from the printer.

In general, according to another embodiment, a drug mixing preparation managing apparatus includes a printer that prints labels; a reader that reads identification information; a communication interface for obtaining information based on the identification information read by the reader; a drug inspection module configured to compare information about a candidate drug for inclusion in a mixed injection with a mixed injection preparation instruction and to determine whether the mixed injection is prepared in accordance with the mixed injection preparation instruction; and a label issue module configured to cause the printer to print a label to be directly or indirectly attached to the mixed injection after the drug inspection module determines that the mixed injection is prepared in accordance with the mixed injection preparation instruction, the label issue module configured to detect whether the label is removed from the printer.

According to another embodiment, there is provided a control method including: in a drug mixing preparation managing apparatus that includes a printer that prints information and a reader that reads identification information, and performs an inspection process of a drug used in drug mixing preparation, performing the drug inspection process on the basis of data of the identification information assigned to a drug assorted to be used in the drug mixing preparation, read by the reader, and data on a drug that is a mixed injection target, acquired in advance; and issuing, using the printer, a label on which an inspection result in the performing of the drug inspection process is written, to be directly or indirectly attached to a drug that is an inspection target, at a timing when the inspection in the performing of the drug inspection process is normally completed or at a timing when abnormality occurs in the inspection.

According to a still another aspect of the embodiment, there is provided a control program, stored in a non-transitory computer-readable medium, for controlling, using a computer, a drug mixing preparation managing apparatus that includes a printer that prints information and a reader that reads identification information, and performs an inspection process of a drug used in drug mixing preparation and causing the computer to function as: a drug inspection unit configured to perform a drug inspection process on the basis of data of the identification information assigned to a drug assorted to be used in the drug mixing preparation, read by the reader, and data on a drug that is a mixed injection target, acquired in advance; and a label issue unit configured to issue, using the printer, a label on which an inspection result by the drug inspection unit is written, to be directly or indirectly attached to a drug that is an inspection target, at a timing when the inspection by the drug inspection unit is normally completed or at a timing when abnormality occurs in the inspection.

Next, preferred exemplary embodiments will be described referring to the accompanying drawings.

FIG. 1 is a block diagram illustrating a schematic configuration of a drug mixing preparation managing system.

A drug mixing preparation managing system 10 includes an electronic medical record server 11 that manages and stores an electronic medical record, an information processing terminal 12 for a doctor to write or edit the electronic medical record or the like, an information processing terminal 13 for a nurse to reference or confirm the electronic medical record managed by the electronic medical record server 11, mixed injection terminals 14 for supporting a mixed injection preparation process by aiding drug sorting on the basis of instruction information (for example, prescription information) included in the electronic medical record, a mobile information processing terminal 18 for a doctor (or the like) that is connected to a communication network 17 through a wireless base station 15 and a public communication network 16, and a pharmacy server 19 that is disposed in a pharmacy and manages drug payment, invoicing, or the like.

In the above configuration, the electronic medical record server 11, the information processing terminal 12, the information processing terminal 13 and the mixed injection terminal 14 are connected to the communication network 17.

Figure 2:
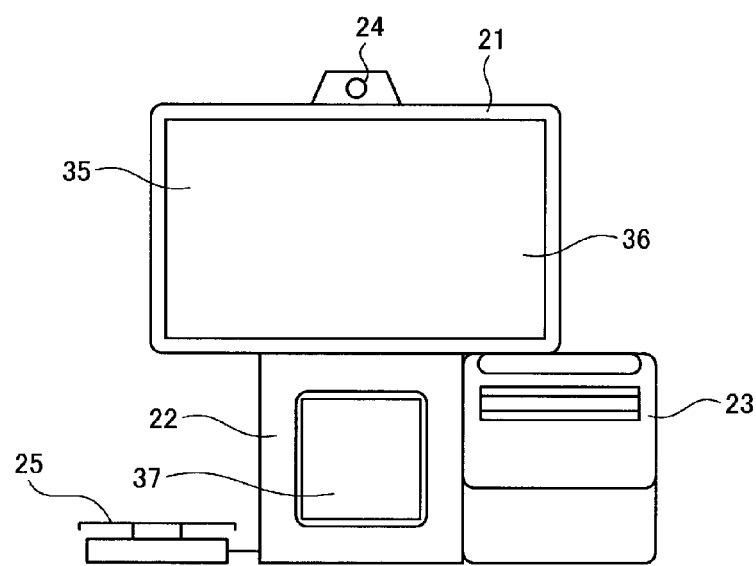
FIG. 2 depicts a front view of a mixed injection terminal according to an embodiment.

FIG. 2 is a front view illustrating the appearance of a mixed injection terminal.

The mixed injection terminal 14 includes a touch panel display 21, through which a user performs various operations, that is capable of displaying various information such as a list of drugs included in mixed injection targets or an inspection state of the drugs to be included in a mixed injection preparation, a device body 22 that has a scanner 37 that is a reader configured as an object scanner that scans an ID of a nurse (or the like) who is a user, a bar code including identification information on a drug, an image of the drug or the like, a printer 23 for printing out various information, a camera 24 that images a work of an operator, and a scale 25 that measures the weight of a drug or other component to be included in a mixed injection preparation.

Figure 3:
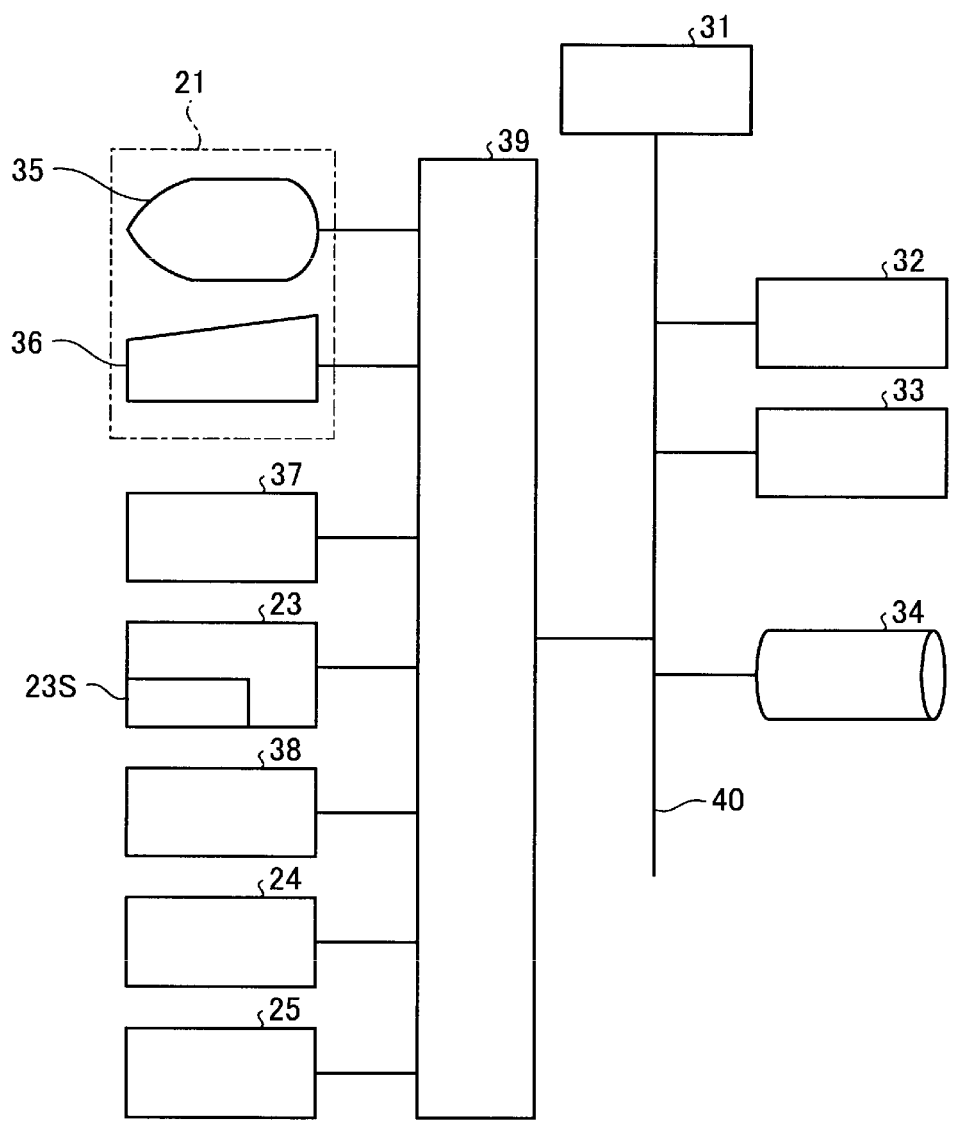
FIG. 3 is a block diagram of a schematic configuration of a mixed injection terminal.

FIG. 3 is a block diagram illustrating a schematic configuration of the mixed injection terminal 14.

The mixed injection terminal 14 includes an MPU 31 that controls the overall operation of the mixed injection terminals, a ROM 32 that stores various data that includes a control program in a non-volatile manner, a RAM 33 that functions as a work area and temporarily stores various data, an external storage unit 34 configured as a hard disk drive or a solid state drive (SSD) capable of storing a large amount of data such as a database, a display 35 and a touch panel 36 that form the touch panel display 21, the scanner 37, the printer 23, and a communication interface 38 that performs a communication interface operation.

Here, the touch panel display 21, the scanner 37, the printer 23 and the communication interface 38 are connected to a bus 40 through an input and output I/O 39. A sensor 23S that detects whether a label, which may be issued with base paper (the backing paper of an adhesive label) attached or issued with base paper detached, is removed, is provided in the vicinity of a label issue port of the printer 23 in this embodiment. The sensor 23S is, for example, a transmissive optical sensor, that detects the presence or absence of the label according to whether the label blocks an optical path.

Further, in the external storage unit 34, images (moving images such as video) captured by the camera 24 from login to logout are stored as a work record, and weights of drugs before and after a mixed injection preparation are measured by the scale 25 and data regarding the difference thereof are also stored as a work record.

The MPU 31, the ROM 32, the RAM 33 and the external storage unit 34, in addition to the communication interface 38, are connected to the bus 40.

Next, an operation of the exemplary embodiment will be described.

Before the mixed injection preparation is prepared and administered, a doctor creates an electronic medical record that includes drug instruction data (for example, prescription data) using the information processing terminal 12 and registers the electronic medical record in the electronic medical record server 11.

In this case, information for specifying drugs that are to be included in the mixed injection and information relating to the amount of each drug are included in the instruction data (for example, prescription data), and an order number for specifying the instruction data is allocated thereto. The order number is sent together with an instruction (so-called mixed injection instruction) to a pharmacist or a nurse or is printed as a symbol code such as a bar code on the instruction.

On the other hand, if an operator such as a nurse who actually sorts the drugs of the mixed injection targets receives the order number, the operator performs a sorting and inspection of the drugs to be included in the mixed injection.

Here, a sorting and inspection process of the mixed injection drugs will be described.

Figure 4:
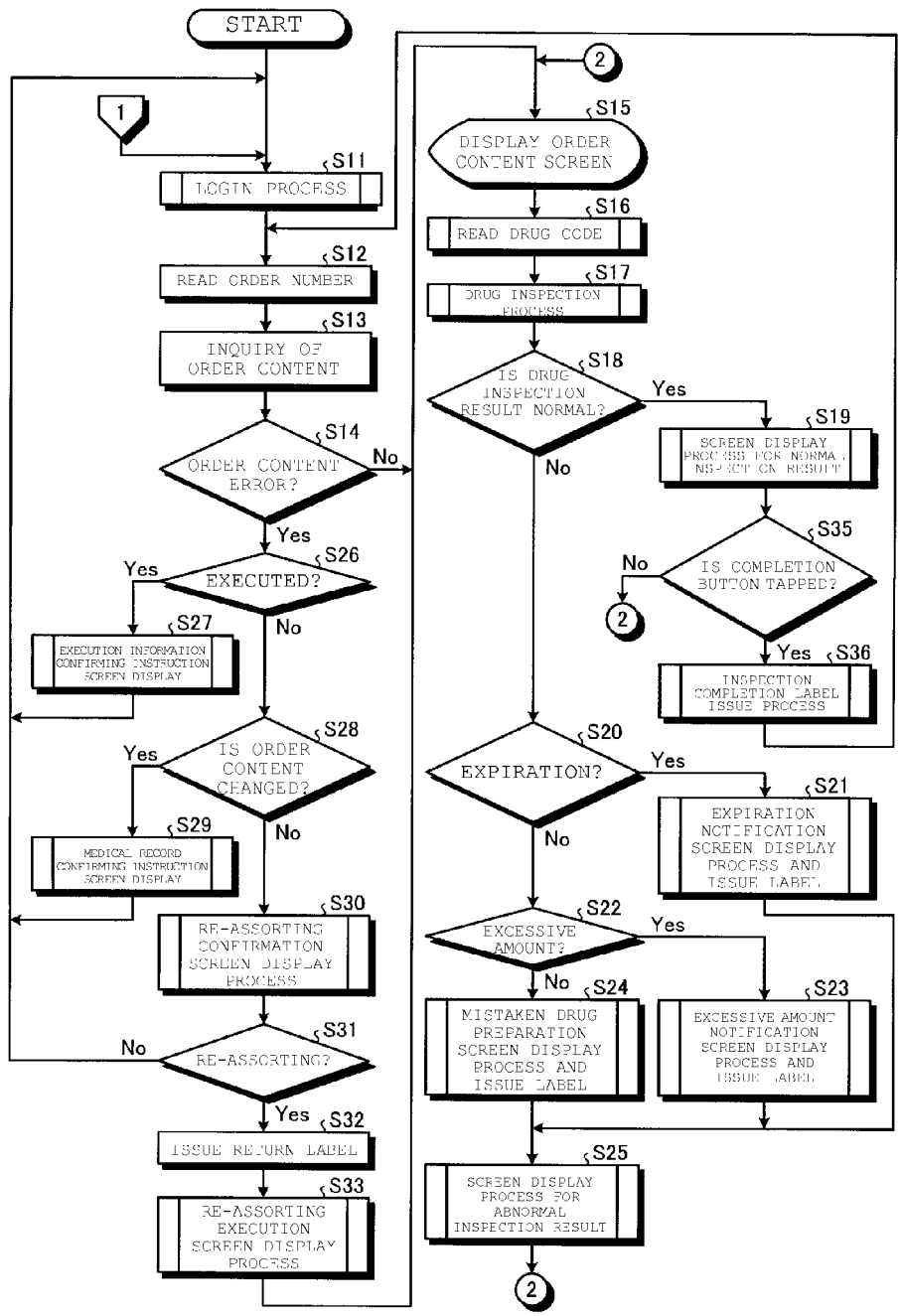
FIG. 4 is a process flowchart of a mixed injection terminal system according to an embodiment.

FIG. 4 is a process flowchart of a mixed injection terminal according to an exemplary embodiment.

In the following description, each operator who is allowed to operate the mixed injection terminal 14 has an ID card, and is able to operate the mixed injection terminal 14 by authentication of the ID card.

On the display 35 of the touch panel display 21 of the mixed injection terminal 14, a login screen is displayed as an initial state.

Figure 5:
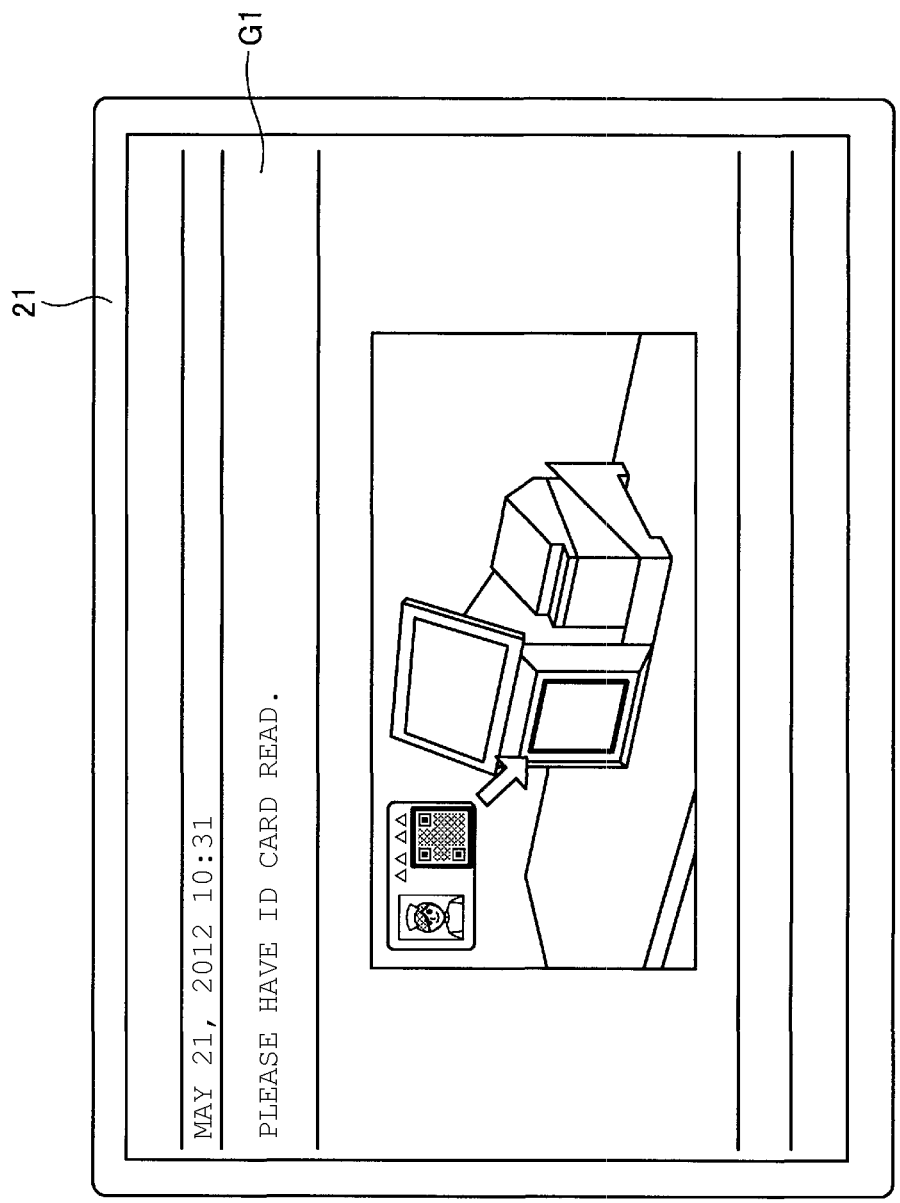
FIG. 5 is a diagram illustrating an example of a login instruction screen.

FIG. 5 is a diagram illustrating an example of a login instruction screen.

As shown in FIG. 5, a guide comment "Please have the ID card read" and a login screen G1 that prompts the scanner 37 to read the ID card are displayed on the login screen.

Accordingly, in order to perform the login process, an operator places the ID card of his/her own in front of the scanner 37 to cause the scanner 37 to read an ID code (step S11).

Figure 6:
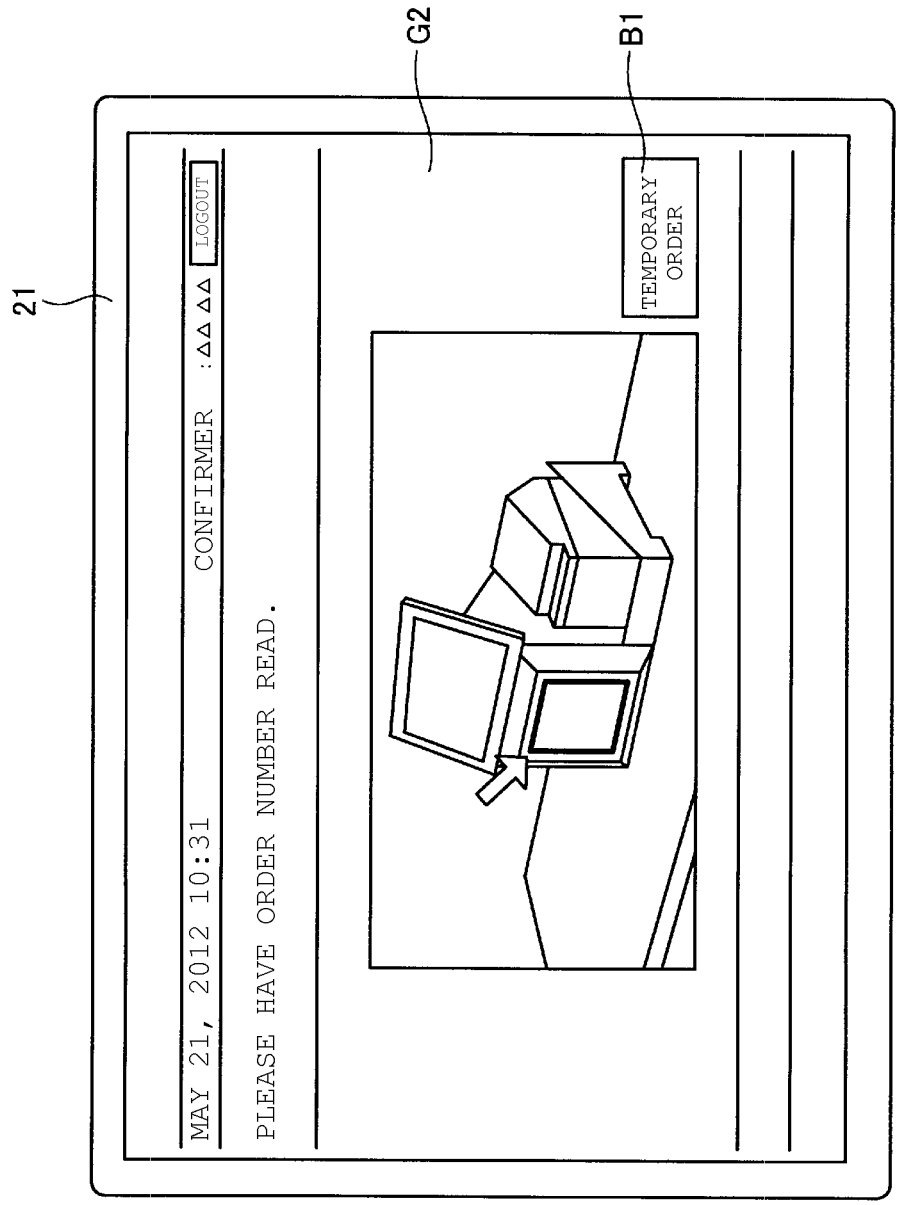
FIG. 6 is a diagram illustrating an example of an order number input screen.

FIG. 6 is a diagram illustrating an example of an order number input screen.

If the ID code is authenticated in the login process, the MPU 31 of the mixed injection terminal 14 displays an order number input screen G2 on a display screen of the display 35 in order to prompt reading of an order number for specifying the mixed injection preparation instructions (prescription), which includes a list of drugs to be included in the mixed injection (step S12).

As shown in FIG. 6, a guide comment "Please have order number read" and a guide image that prompts the scanner 37 to read the order number are displayed on the order number input screen G2. Further, when the guide image is displayed, a temporary order button B1 for temporarily making an order without order number allocation is displayed.

Thus, if the operator causes the order number to be read by the scanner 37, the MPU 31 of the mixed injection terminal 14 makes an inquiry about content of the order to the electronic medical record server 11 or the pharmacy server 19 through the communication interface 38 and the communication network 17 (step S13).

Subsequently, the MPU 31 of the mixed injection terminal 14 determines whether an error occurs in the order content on the basis of response of the electronic medical record server 11 or the pharmacy server 19 with respect to the inquiry of the order content (step S14).

In the determination of step S14, if the response of the electronic medical record server 11 or the pharmacy server 19 is a transmission of a list including the drugs to be included in the mixed injection preparation corresponding to the order number, this means that there is no error in the order content (No in step S14), and thus, the MPU 31 displays an order content display screen G3 on the basis of the obtained list data (step S15).

Figure 7:
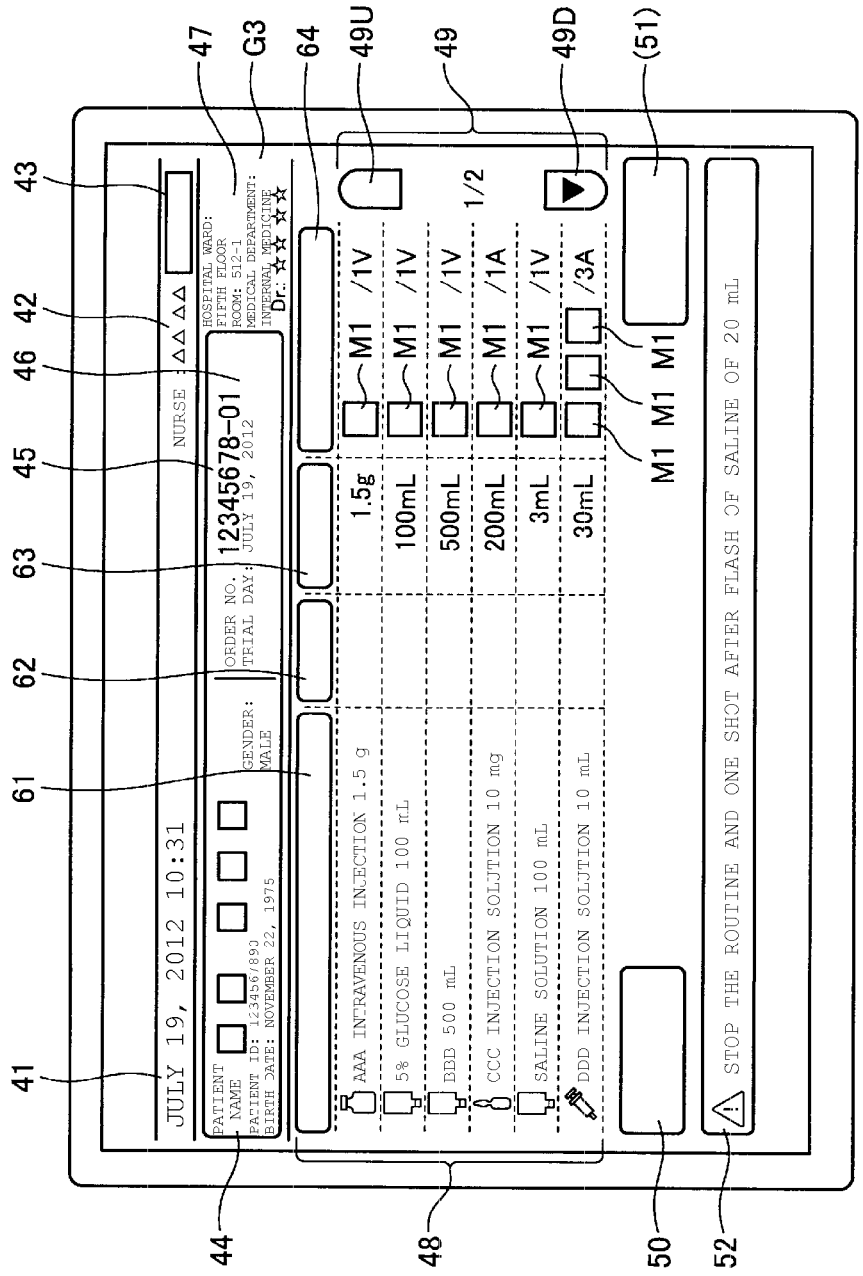
FIG. 7 is a diagram illustrating an example of an order content display screen.

FIG. 7 is a diagram illustrating a display example of an order content display screen.

The order content display screen G3 is classified into a date information display area 41, an operator name display area 42, a logout button 43, a patient information display area 44, an order number display area 45, a trial day display area 46, a patient related information display area 47, a drug list display area 48, a list scroll button display area 49, a stop button 50, a completion button 51, and a comment display area 52.

The date information display area 41 is an area where the time and date of the mixed injection preparation is displayed.

The operator name display area 42 is an area where the name of an operator who is inspecting the drugs of the mixed injection preparation is displayed.

The logout button 43 is a button through which the operator is logged out.

The patient information display area 44 is an area where information for specifying a patient to whom the drugs are to be administered is displayed. Specifically, name, ID, birth date and gender of the patient are displayed.

The order number display area 45 is an area where an order number obtained in step S12 is displayed.

The trial day display area 46 is an area where a trial day (that is, the date when the drugs are to be administered to the patient) is displayed. The trial day is designated in the electronic medical record.

The patient related information display area 47 is an area where information relating to the patient is displayed. Specifically, ward information, hospital room information, medical care information and a name of a doctor in charge are displayed.

The drug list display area 48 includes a drug name display area 61 that displays names of drugs in the prescribed mixed injection preparation, a unit number display area 62 where when the amount of drug prescribed is designated the units of the dose (amount in which a drug shows a specific biological effect) is displayed, the number of units to be administered is displayed, an instructed amount display area 63 where when the amount of drug prescription is designated as an instructed amount (weight or volume), the amount to be prescribed (weight or volume) is displayed, and a necessary number display area 64 where the number of a drug (the number of an ampoule, a vial or the like) necessary for satisfying the unit number designated by the unit number display area 62 or the instruction amount designated by the instruction amount display area 63 is displayed in a line by the same number of marks (icons, patterns) M1 as the number of the drug and the number of the drug is displayed as a numerical value.

In the example in FIG. 7, for example, as shown in the top part of the list, since a drug name "1.5 g for AAA intravenous injection" (container type: vial) has an instructed amount of 1.5 g, in the necessary number display area, one mark M1 that indicates that it is necessary to use one vial is disposed, and "/1V" that indicates that the total number corresponds to one vial is displayed. Further, as shown in the bottom part of the list, since a drug name "DDD injection of 10 mL" (container type: ampoule) has an instructed amount of 30 mL, three marks M1 that indicate that it is necessary to use three ampoules are disposed side by side, and "/3A" that indicates that the total number corresponds to 3 ampoules is displayed.

In the list scroll button display area 49, when a list of all drugs cannot be displayed in the drug list display area 48 at a time, an up-scroll button 49U for scrolling the list upward, and a down-scroll button 49D for scrolling the list downward are disposed. In the example in FIG. 7, since it is impossible to scroll the list upward, the up-scroll button 49U represents a gray-out display state, which represents a non-operable state.

The stop button 50 is a button for instructing the stop of the inspection process for the drugs of the mixed injection preparation.

The completion button 51 is a button that is in an operable state when the entire inspection process of the drugs of the mixed injection targets is terminated, and enters a gray-out display state since the inspection process is not terminated in FIG. 7, which represents a non-operable state.

The comment display area 52 is an area where when a comment to be noted in mixed injection of the drugs of the mixed injection targets is registered, the comment is displayed.

In a state where the order content display screen G3 in FIG. 7 is displayed, in order to perform the inspection process of the drugs of the mixed injection target, an operator causes the scanner 37 to read an GS1 data bar (GS1-RSS code: medical drug bar code) indicated in a container or a cover of a drug that is to be included in the mixed injection (step S16).

Thus, the MPU 31 performs the drug inspection process on the basis of the content of the drug list and the GS1 data bar read in step S16 (step S17).

Figure 8:
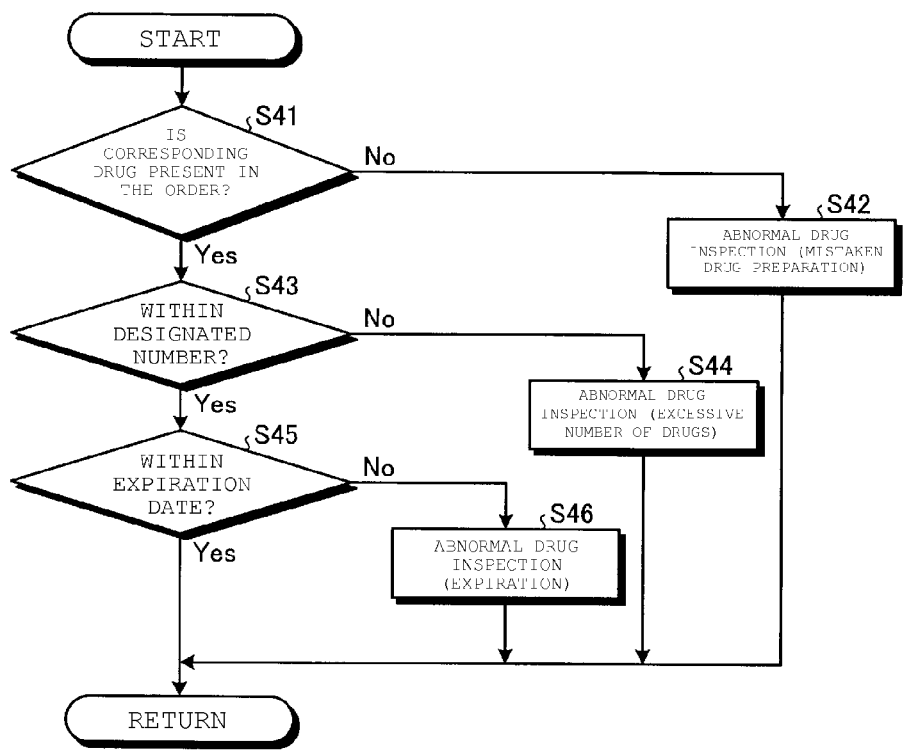
FIG. 8 is a flowchart of a drug inspection process.

FIG. 8 is a processing flowchart of the drug inspection process.

First, the MPU 31 determines whether the drug corresponding to the read GS1 data bar is included in the order (step S41).

In the determination in step S41, if the drug corresponding to the read GS1 data bar is not included in the order (No in step S41), the MPU 31 determines this case as an abnormal drug inspection of a mistaken drug preparation in which a wrong drug that is not included in the order is prepared (step S42), and terminates the drug inspection process. Then, the procedure proceeds to step S18.

In the determination of step S41, if the drug corresponding to the read GS1 data bar is included in the order (Yes in step S41), the MPU 31 determines whether the number (e.g., dosage level) of the drug corresponding to the read GS1 data bar is within a designated number (step S43).

In the determination of step S43, if the number of the drug corresponding to the read GS1 data bar is not within the designated number, that is, if the number of the drug exceeds the designated number (No in step S43), the MPU 31 determines this case as an abnormal drug inspection of an excessive drug number in which the drug of an amount larger than the amount of the drug to be prescribed is prepared (step S44), and terminates the drug inspection process. Then, the procedure proceeds to step S18.

In the determination of step S43, if the number of the drug corresponding to the read GS1 data bar is within the designated number (Yes in step S43), the MPU 31 determines whether the drug corresponding to the read GS1 data bar is within an expiration date (step S45).

In the determination of step S45, if the drug corresponding to the read GS1 data bar is not within the expiration date, that is, if the expiration date of the drug has passed (No in step S45), the MPU 31 determines this case as an abnormal drug inspection of expiration in which the drug cannot be used in mixing injection due to expiration of the expiration date (step S46), and terminates the drug inspection process. Then, the procedure proceeds to step S18. If the drug corresponding to the read GS1 data bar is within the expiration date (Yes in step S45), the MPU 31 terminates the process as it is. Then, the procedure proceeds to step S18.

Figure 9:
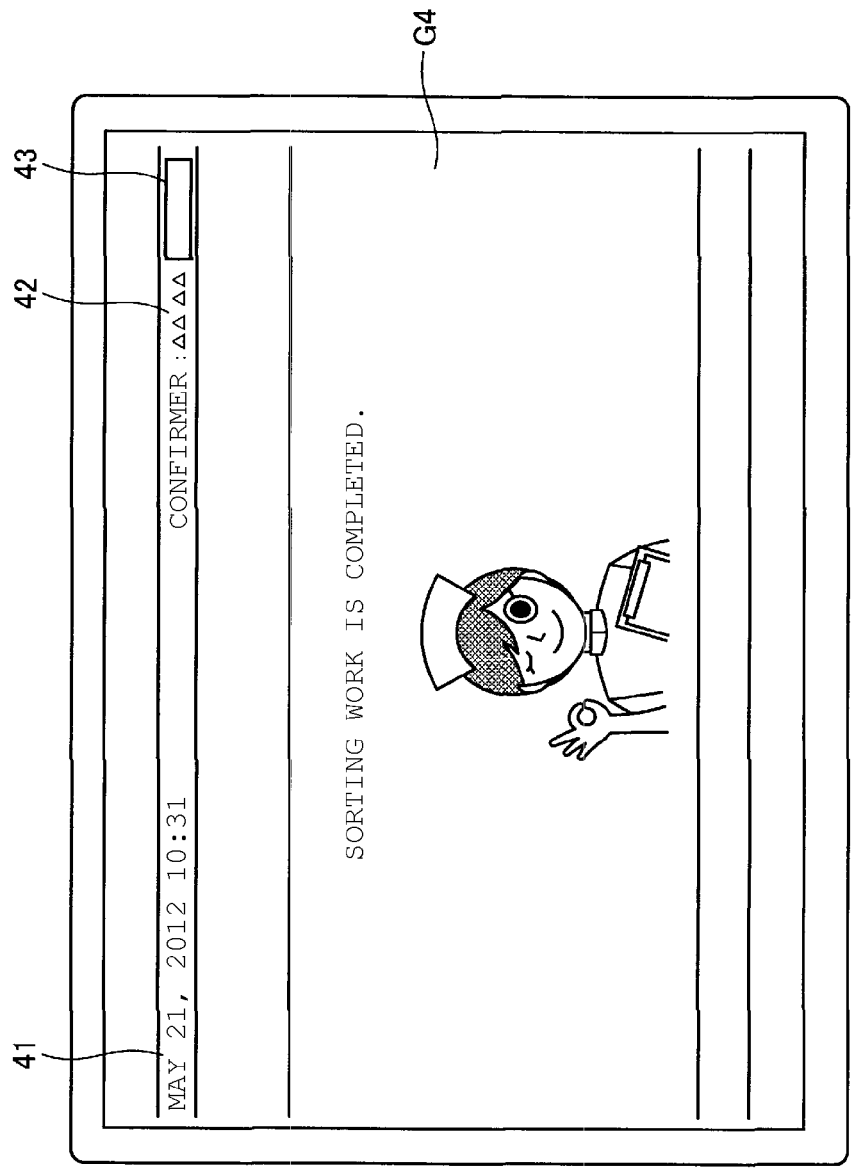
FIG. 9 is a diagram illustrating an example of an inspection completion screen.

FIG. 9 is a diagram illustrating an example of an inspection completion screen.

A message "The assorting work has been completed" is displayed on an inspection completion screen G4, and thus, the operator may easily detect that the sorting work of the drugs to be included in the mixed injection and the inspection process of the drugs have been correctly completed.

On the other hand, in the determination of step S47, if the sorting of all the drugs is not completed yet (No in step S47), the MPU 31 determines whether the drug inspection result of a drug that is to be included in the mixed injection preparation is normal (step S18).

In the determination of step S18, if the drug inspection result is normal (Yes in step S18), a screen display process for the normal inspection result is performed (step S19). Then, until the completion button 51 is tapped (No in step S35), the procedure proceeds to step S15 again, to reflect the inspection result display screen in the display of the order content display screen.

Next, an example of an inspection result display screen will be described referring to FIG. 10.

Figure 10:
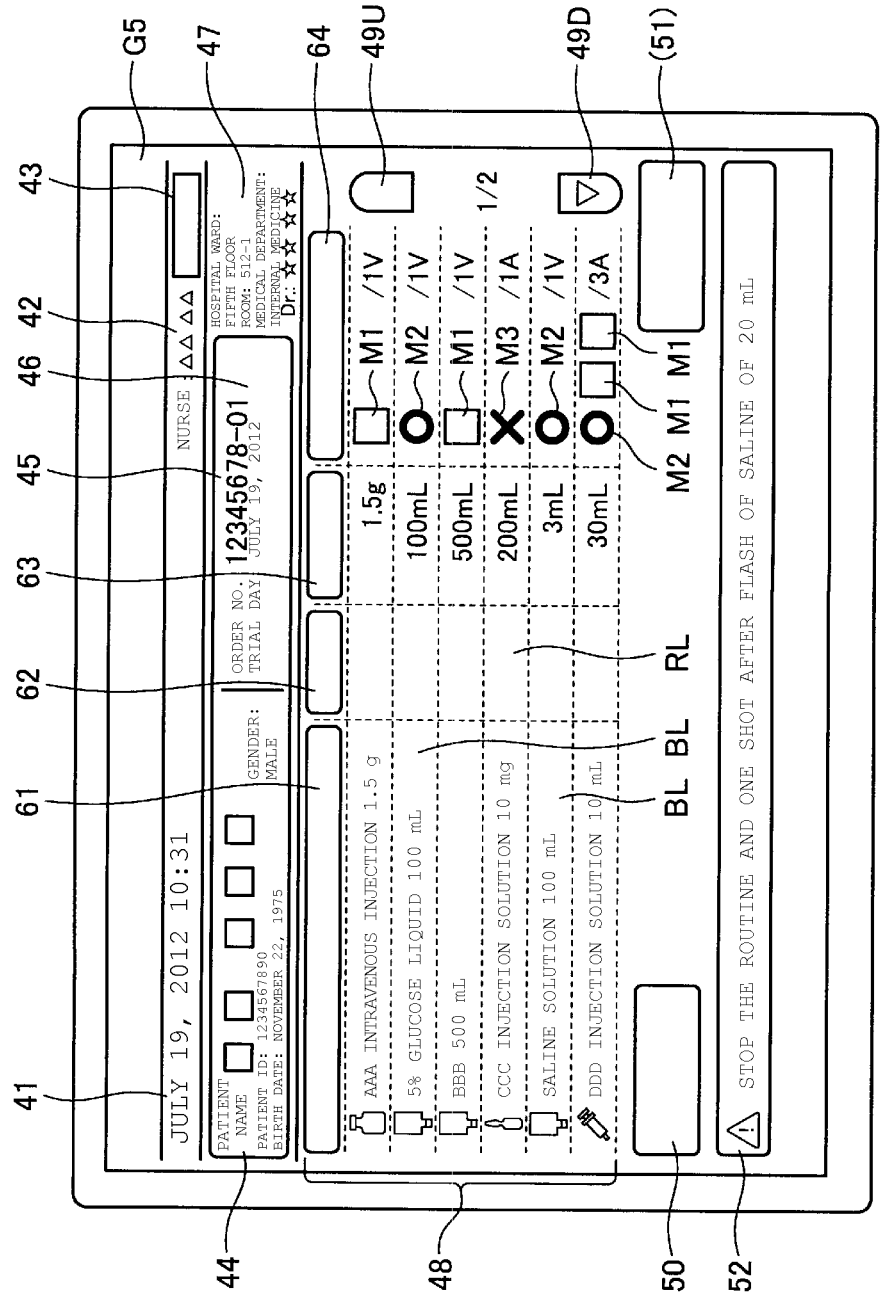
FIG. 10 is a diagram illustrating an example of an inspection result display screen.

In the case of an example of an inspection result display screen G5 in FIG. 10, for example, if the read drug code is a drug name "5% glucose liquid of 100 mL", a mark M2 that represents that one bag is assorted ("mark ○" in FIG. 10) at a time point shown in FIG. 7, instead of one mark M1 that represents that it is necessary to use one bag in total, is displayed in the instructed amount display area 63 of a section of a drug name "5% glucose liquid of 100 mL" that is present in the second row from the top of the list. Further, for example, the section of the drug name "5% glucose liquid of 100 mL" is changed into a blue line display BL that represents that the drug corresponding to the section is entirely sorted.

Further, if the read drug code corresponds to a drug name "DDD injection solution", a mark M2 that represents that one ampoule/bottle/bag is assorted ("mark ○" in FIG. 10) at a time point shown in FIG. 7, instead of the leading mark M1 among three marks M1 that represent that it is necessary to use three ampoule in total, is displayed in the instructed amount display area 63 of a section of a drug name "DDD injection solution" that is present in the sixth row from the top of the list. In this case, since the necessary number of the drug is not sorted, at this point, the color of the section of the drug name "DDD injection solution" is not changed compared with the case of FIG. 7. That is, once the prescribed number of units of a prescribed drug are scanned, the displayed drug name changes in display state (e.g., to a blue line display) to indicate the correct number of units have been sorted.

As described above, if the necessary number of the drug among the drugs displayed in the drug list is sorted, since the section enters a state indicating the fact (in this example, blue line display BL), the operator may easily determine whether assorting is completed for each drug.

Further, in the instructed amount display area 63, since only the marks of which the total number is already assorted is replaced with different marks for display compared with the case before the sorting, the operator may easily recognize how many times the sorting should be performed from now on.

Figure 11:
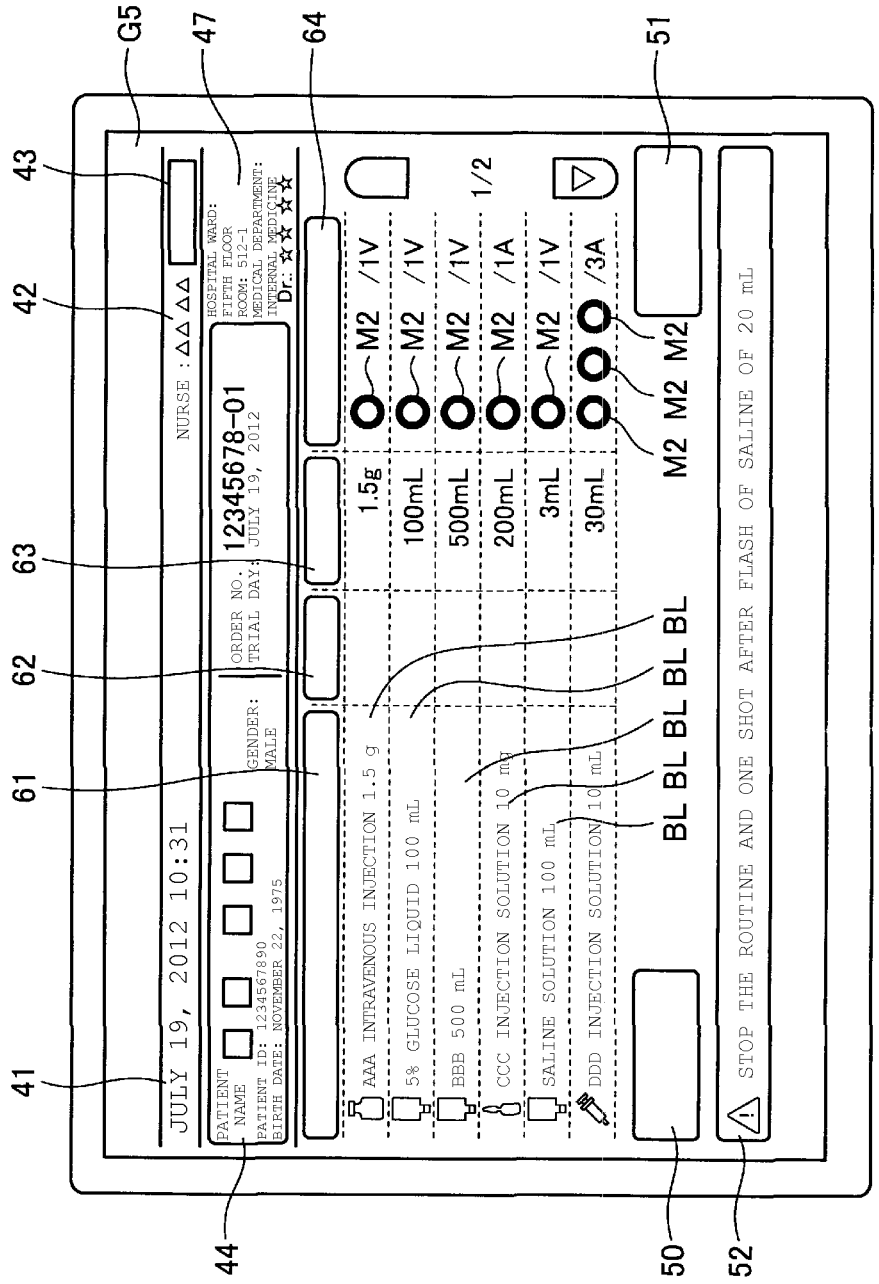
FIG. 11 is a diagram illustrating an example of an inspection result display screen after all drugs are inspected and confirmed.

FIG. 11 is a diagram illustrating an example of an inspection result display screen when all the drugs are assorted. If all the inspection processes are normal and all the drugs are assorted, the marks M2 that represent that the drugs are assorted (in FIG. 11, mark "○") at the time point shown in FIG. 7, instead of the marks M1, are displayed in the instructed amount display area 63 corresponding to all the drugs. Further, all the drug sections are changed into the blue line displays BL that indicate all the drugs corresponding to the sections are assorted. Further, the completion button 51 for completing the process and the stop button 50 for stopping the process are displayed.

The MPU 31 determines whether the completion button 51 displayed in FIG. 11 is tapped (step S35 in FIG. 4). If the MPU 31 determines that the completion button 51 is tapped (Yes in step S35), the MPU 31 executes an inspection completion label issue process (step S36). The inspection completion label issue process is performed by executing the process of the flowchart in FIG. 12.

Figure 12:
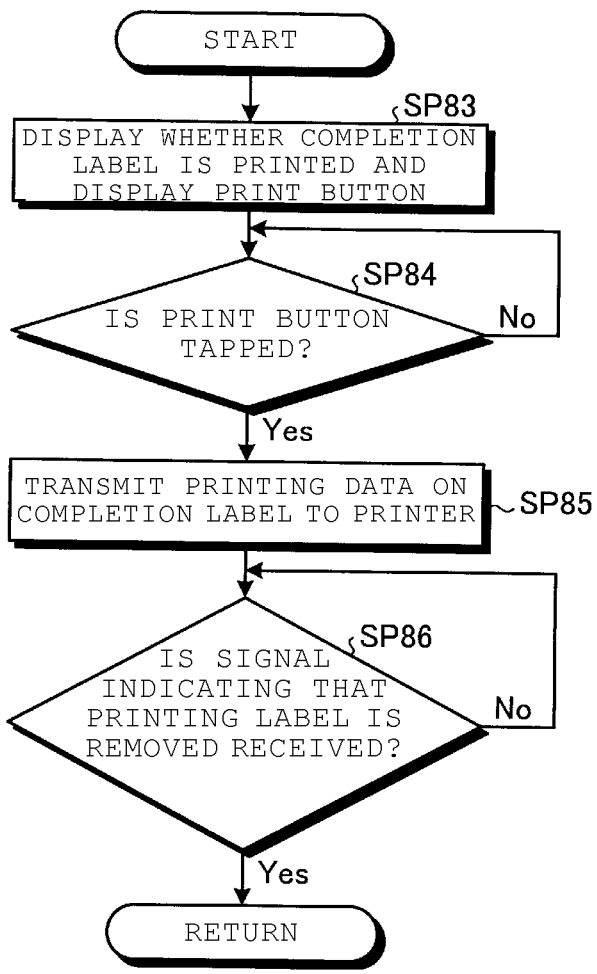
FIG. 12 is a flowchart of a label issue process when all drugs are inspected and confirmed.
Figure 15:
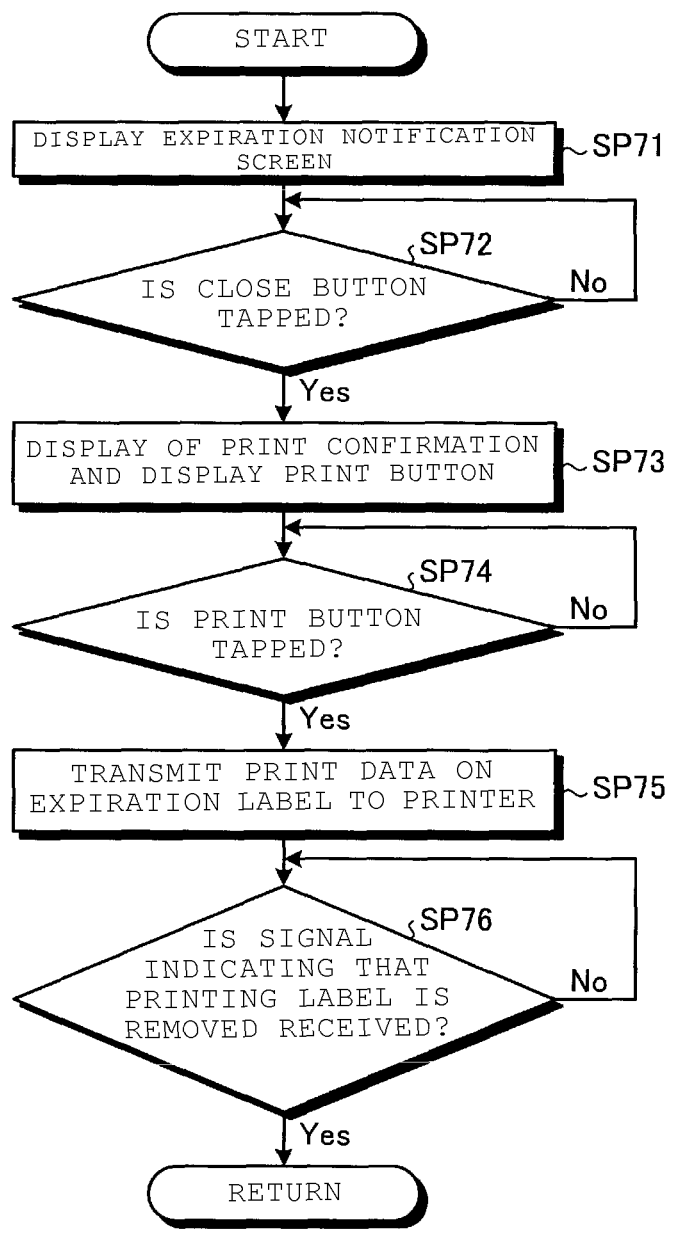
FIG. 15 is a flowchart of a label issue process when an expiration date of a component has passed.

In FIG. 12, a message "Is an inspection completion label printed?" and a print button are displayed on the display 21 (step S83). FIG. 13 is a display screen according to step S83, which shows an order number 101, a message 111 "Is an inspection completion label printed?", a print button 106 through which printing is executed, and the like. The MPU 31 determines whether the print button 106 is tapped (step S84), and waits until the print button 106 is tapped (No in step S84). If it is determined that the print button 106 is tapped (Yes in step S84), the MPU 31 transmits completion label print data to the printer 23 (step S85).

If the printer 23 receives the print data, the printer 23 prints a label 115 shown in FIG. 14. In FIG. 14, on the label 115, the order number 101, a display 112 of "mixed injection" that indicates that the drug inspection is completed and the drug mixed injection is completed, a name 113 of a drug obtained by mixed injection, a bar code 114, for example, that is obtained by coding the order number, and individual information 119 such as a patient name, birth date, age and gender are printed. The bar code 114 is an example, and a different code (two-dimensional code, for example) other than the bar code may be used. Further, if the label 115 is a label issued through a re-assorting process, "re-assorting" may be displayed on the label.

The printer 23 issues the printed label 115 through a label issue port. The issued label 115 is detached from the printer 23 by a person, in this example, and is then attached to a container or a bag in which the inspected drug (mixed injection preparation) is stored. In the vicinity of the label issue port, the sensor 23S that detects the presence or absence of the issued label 115 is provided. When the label 115 is not removed, the sensor 23S outputs a detection signal that indicates that the label 115 is present, and when the label 115 is removed, the sensor 23S outputs a detection signal that indicates that the label 115 is not present.

The MPU 31 determines whether the detection signal that indicates that the label 115 is removed and the label 115 is not present is output from the sensor 23S (step S86), and waits until it is determined that the signal is output (No in step S86). If it is determined that the signal is output (Yes in step S86), an inspection completion screen for indicating that all the inspections are completed and the drugs are properly inspected is displayed (step S87). Then, the screen display process for the normal inspection result is completed.

If it is determined that the completion button 51 is not tapped (No in step S35), the MPU 31 causes the procedure to proceed to step S15 again. Then, in a state where the order content display screen is displayed at that time, in order to perform the inspection process of the drugs of the mixed injection target, the operator causes the scanner 37 to read a GS1 data bar (GS1-RSS code: medical drug bar code) indicated in a container or a cover of the assorted drug that is the mixed injection target (step S16). Then, the same processes are repeatedly performed.

As described above, in the present exemplary embodiment, when all the drugs are normally sorted, since necessary print data such as a message 112 "mixed injection" that represents that the drug inspection is completed and the drug mixed injection is completed or a bar code 114 in which the name of each drug is printed are transmitted and the label 115 is printed by the printer 23 for issue, the label 115 is issued at the optimal timing, and thus, it is possible to attach the label 115 to the mixed injection container or the bag immediately after the inspection is completed. Regardless of the present exemplary embodiment, it is preferable that a message that enables determining that drugs are normally sorted be printed on the label 115.

Further, since the MPU 31 can be set to allow execution of the next process only under the condition that it is determined that the label has been removed, it is possible to prevent omission of the label attachment.

Since the bar code 114 obtained by coding the order number is printed on the label 115, instead of displaying the inspection completion screen under the condition that the signal of the sensor 23S is received, the inspection completion screen may be displayed under the condition that the bar code 114 is read by the scanner 37 and the order number 101 included in the read bar code matches with the order number 101 of the drug mixed injection.

In the present exemplary embodiment, the order number 101 is coded as the bar code 114, but other different management numbers or the like may be used. In the present exemplary embodiment, the bar code 114 is read by the scanner 37, but for example, identification information stored in an RFID embedded in the label may be read by an RFID reader for each drug or for all the drugs in a batch. Further, the number issued in a label by these bar code types and RFID may be used for disposal management of drugs or the like (including blood transfusion pack).

On the other hand, in the determination of step S18, if the drug inspection result is abnormal (No in step S18), the MPU 31 determines whether the reason of the abnormal drug inspection result is expiration of the expiration date (step S20).

In the determination of step S20, if the reason of the abnormal drug inspection result is expiration of the expiration date (Yes in step S20), the MPU 31 performs an expiration notification screen display process and the label issue process (step S21).

The expiration notification screen display process and the label issue process (step S21) will be described referring to FIGS. 15 to 18.

Figure 16:
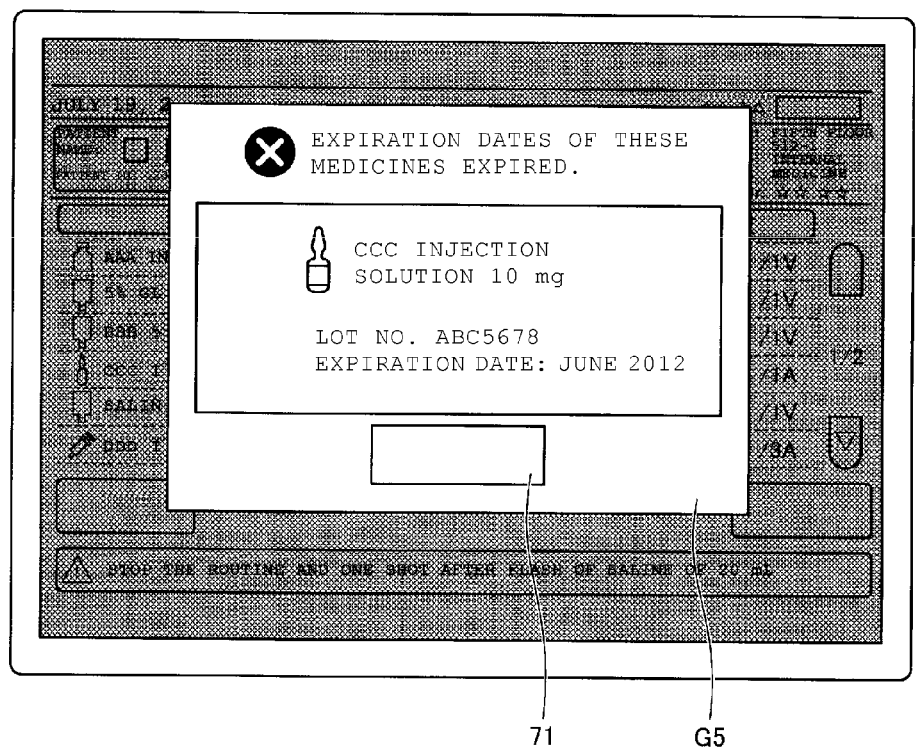
FIG. 16 is a diagram illustrating an example of an expiration notification screen.
Figure 17:
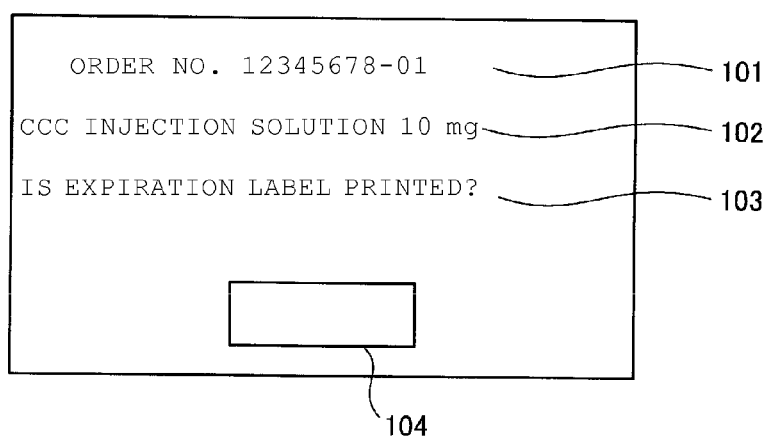
FIG. 17 is an example of a label issue screen when an expiration date has passed.
Figure 19:
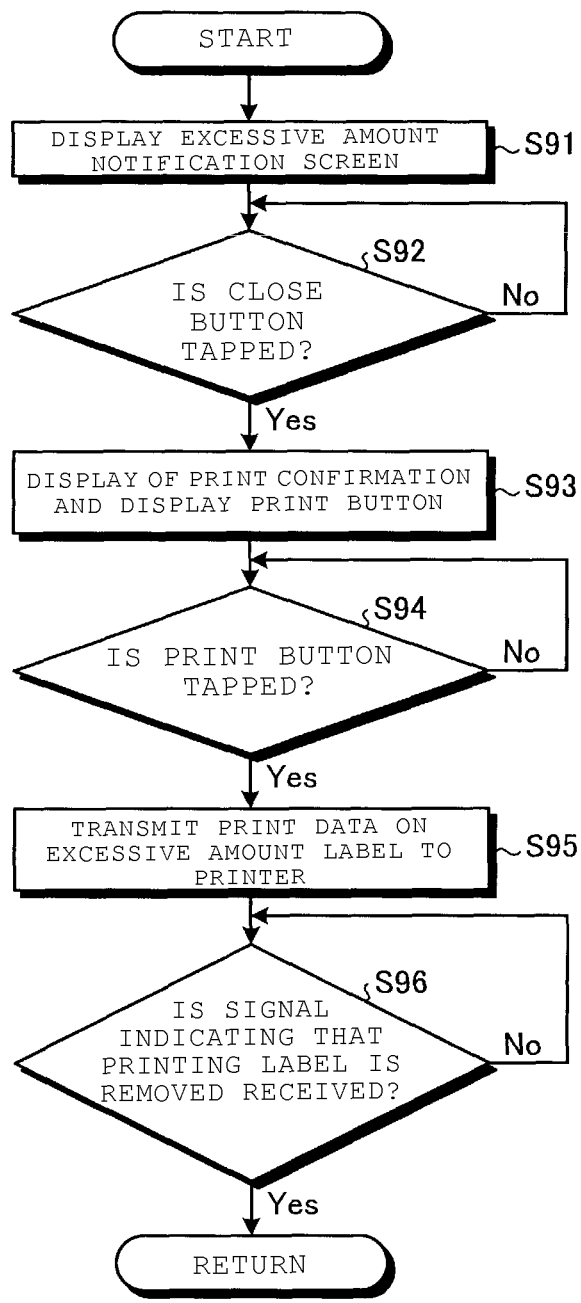
FIG. 19 is a flowchart of a label issue process when the amount of a component is excessive.

As a result of the above-described drug inspection process (step S18), if it is determined that the expiration date expires (Yes in step S20), an expiration notification screen G5 shown in FIG. 16 is displayed (step S71).

In FIG. 16, on the expiration notification screen G5, if there is a message "Expiration date of the medicine expires", and for example, a name of the drug of which the expiration date expires is "CCC injection solution of 100 mg", the drug name "CCC injection solution of 100 mg", and its lot number and expiration date are displayed (step S70). Further, on the expiration notification screen G5, a "close" button 71 is displayed.

If the operator confirms the content and taps the "close" button 71 displayed on the expiration notification screen G5, the MPU 31 determines whether the "close" button 71 is tapped (step S71). If it is determined that the "close" button 71 is tapped (Yes in step S71), the MPU 31 displays printing confirmation shown in FIG. 17 and displays a print button 104 (step S72). In the printing confirmation display, the order number 101, a drug name 102 of the drug of which the expiration date is inspected as expiration, and a confirmation message 103 on whether to print are displayed. The MPU 31 waits until the print button 104 is tapped (waiting occurs while No in step S73), and if the print button 104 is tapped (Yes in step S73), the MPU 31 transmits print data of the label to the printer 23 (step S74).

If the printer 23 receives the print data based on step S74, the printer 23 prints a label 107 shown in FIG. 18. On the label 107, the order number 101, a message 105 "expiration of the expiration date" that indicates that the expiration date of the drug expires, information 106 about the drug, a bar code 108 that is obtained by coding the order number 101, and individual information 109 such as a patient name, birth date, age and gender are printed.

The printer 23 issues the printed label 107 through the label issue port. In the vicinity of the label issue port, the sensor 23S detects the presence or absence of the issued label 107 according to whether the issued label 107 is detached. When the label 107 is not removed, the sensor 23S outputs a detection signal that indicates that the label 107 is present, and when the label 107 is removed, the sensor 23S outputs a detection signal that indicates that the label 107 is not present.

The MPU 31 determines whether the detection signal that indicates that the label 107 is removed and the label 107 is not present is output from the sensor 23S (step S75), and waits (No in step S75) until it is determined that the signal is output. If it is determined that the signal is output (Yes in step S75), a screen display process for the abnormal inspection result shown in FIG. 10 is executed, for example (step S25 in FIG. 4).

As described above, in the present exemplary embodiment, when the MPU 31 determines when the expiration date expires, since the label on which the message that represents that the expiration date of the drug expires is printed is issued, it is possible to attach the expiration label to the drug at an optimal timing. Regardless of the present exemplary embodiment, it is preferable that a message that reports that the expiration date of the drug be printed on the label 107.

Further, since the MPU 31 is able to execute the next process only under the condition that it is determined that the label is removed and the label is not present, it is possible to prevent omission of the label attachment.

Since the bar code 108 obtained by coding the order number 101 is printed on the label 107, instead of displaying the inspection result screen under the condition that the signal of the sensor 23S is received, the inspection result screen may be displayed under the condition that the bar code 108 is read by the scanner 37 and the order number included in the read bar code matches with the order number 101 of the drug mixed injection. Effectively, the reading of the printed bar code 108 indicates the label 107 has been removed from the printer 23. In the present exemplary embodiment, the order number 101 is coded as the bar code 114, but a different management number may be bar-coded. Coding schemes other than bar-coding may be used. Different identification information (for example, identification information stored in an RFID embedded on the label) may be read by an RFID reader for each drug or for all the drugs at a batch. Further, the number issued in a label by these bar codes and RFID may be used for disposal management of drugs or the like (including blood transfusion pack).

Next, in the determination of step S20, if the reason for the abnormal drug inspection result is not the expiration (No in step S20), the MPU 31 determines whether the reason for the abnormal drug inspection result is an excessive amount (the amount of the drug exceeds the necessary amount) (step S22).

In the determination of step S22, if the reason for the abnormal drug inspection result is an excessive amount (Yes in step S22), the MPU 31 performs an excessive amount notification screen display process (step S23).

The excessive amount notification screen display process and the label issue process (step S23) will be described referring to FIGS. 19 to 22.

Figure 20:
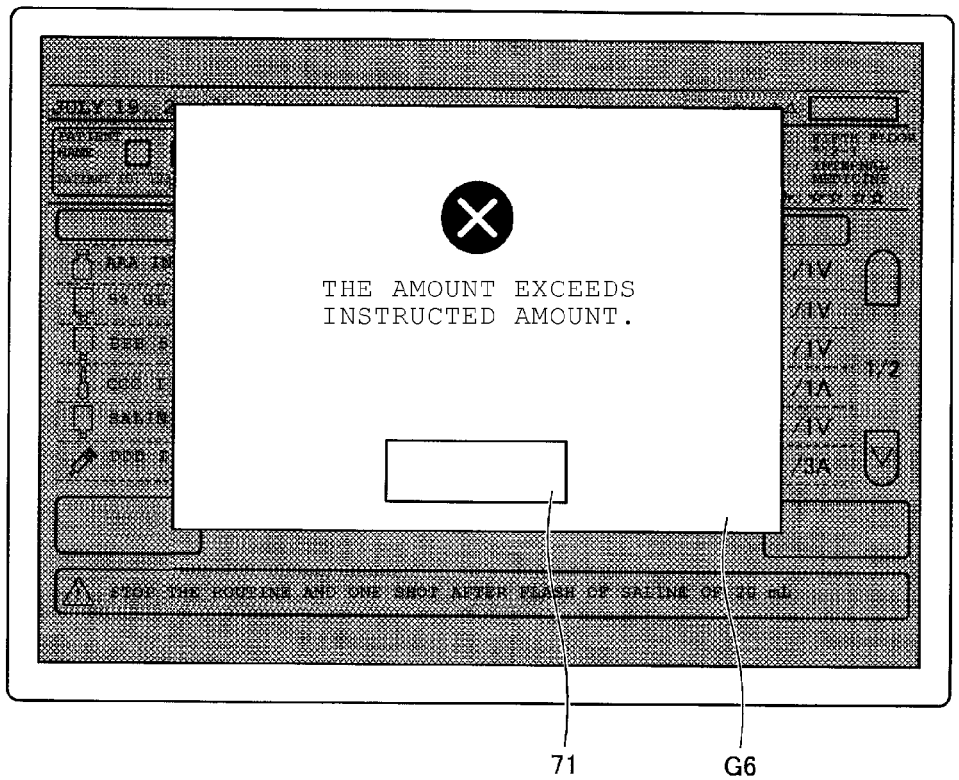
FIG. 20 is a diagram illustrating an example of an excessive amount notification screen.
Figure 21:
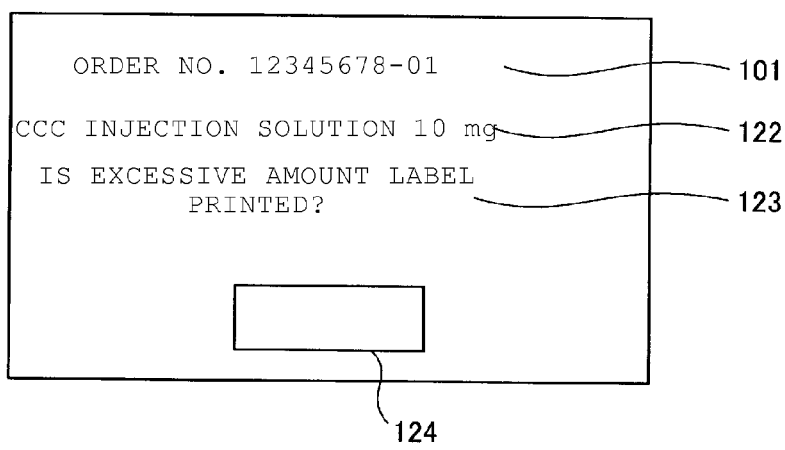
FIG. 21 is an example of a label issue screen when the amount of a component is excessive.
Figure 23:
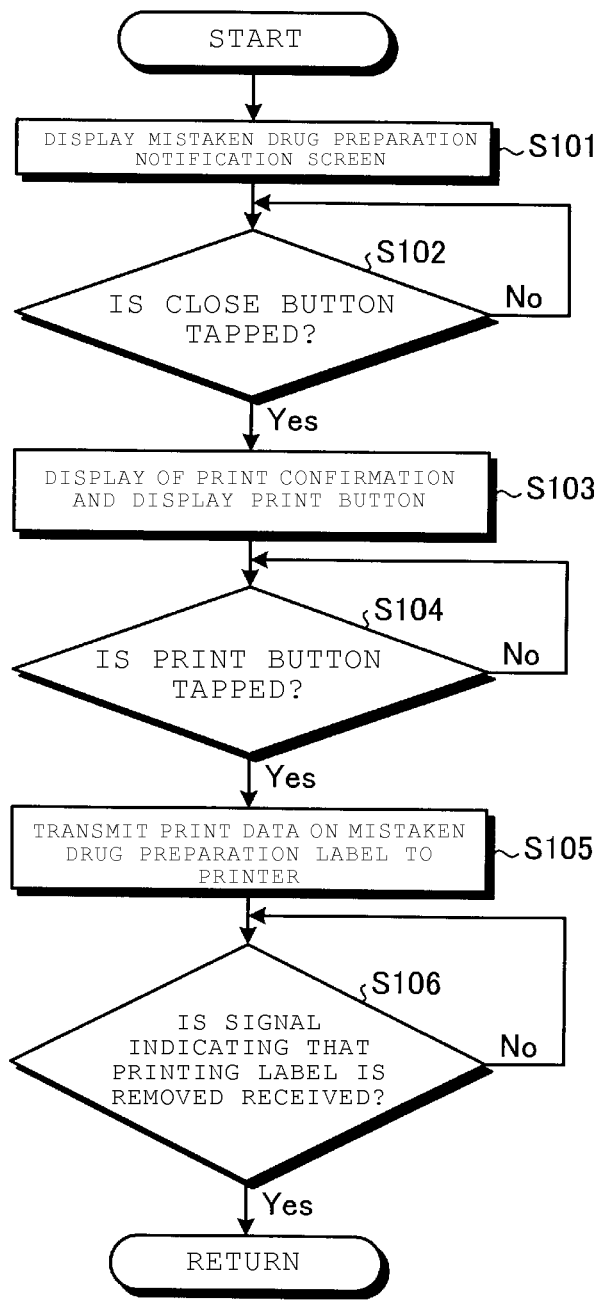
FIG. 23 is a flowchart of a label issue process when a drug is mistakenly selected by an operator.

As a result of the above-mentioned drug inspection process (step S18), if it is determined that the amount is excessive (No in step S20, and Yes in step S22), an excessive amount notification screen G6 shown in FIG. 20 is displayed (step S91).

In FIG. 20, a message "The amount exceeds the instructed amount" is displayed on the excessive amount notification screen G6. Further, the "close" button 71 is displayed on the excessive amount notification screen G6.

If the operator confirms the content and taps the "close" button 71 displayed on the excessive amount notification screen G6, the MPU 31 determines whether the "close" button 71 is tapped (step S92). If it is determined that the "close" button 71 is tapped (Yes in step S92), the MPU 31 displays printing confirmation shown in FIG. 21 and displays a print button 124 (step S93). In the printing confirmation display, the order number 101, a drug name 122 of the drug of which the amount is inspected as being excessive, and a confirmation message 123 on whether to print are displayed. The MPU 31 waits (No in step S94) until the print button 124 is tapped, and if the print button 124 is tapped (Yes in step S94), the MPU 31 transmits print data of the label to the printer 23 (step S95).

If the printer 23 receives the print data based on step S95, the printer 23 prints a label 127 shown in FIG. 22. On the label 127, the order number 101, a message 125 "excessive amount" that indicates that the amount of the drug is excessive, information 126 about the drug, a bar code 128 that is obtained by coding and printing the order number 101, and individual information 129 such as a patient name, birth date, age and gender are printed.

The printer 23 issues the printed label 127 through the label issue port. In the vicinity of the label issue port, the sensor 23S detects the presence or absence of the issued label 127. When the label 127 is not removed, the sensor 23S outputs a detection signal that indicates that the label 127 is present, and when the label 127 is removed, the sensor 23S outputs a detection signal that indicates that the label 127 is not present.

The MPU 31 determines whether the detection signal that indicates that the label 127 is removed and the label 127 is not present is output from the sensor 23S (step S96), and waits until it is determined that the signal is output (No in step S96). If it is determined that the signal is output (Yes in step S96), the screen display process when the inspection result shown in FIG. 10 is abnormal is executed, for example (step S25 in FIG. 4).

As described above, in the present exemplary embodiment, when the MPU 31 determines that the amount is excessive, since the label 127 on which the message that represents that the amount of the drug is excessive is printed is issued, it is possible to attach the excessive amount label to the drug at an optimal timing. Regardless of the present exemplary embodiment, it is preferable that a message that enables determining that the amount of the drug is excessive be printed on the label 127.

Further, since the MPU 31 is able to execute the next process under the condition that it is determined that the label is removed and the label is not present, it is possible to prevent omission of the label attachment.

Since the bar code 128 obtained by coding the order number 101 is printed on the label 127, instead of displaying the inspection result screen under the condition that the signal of the sensor 23S is received, the inspection result screen may be displayed under the condition that the bar code 128 is read by the scanner 37 and the order number included in the read bar code 128 matches with the order number 101 of the drug mixed injection.

In the present exemplary embodiment, the order number 101 is coded as the bar code 128, but a different management number may be bar-coded. Coding schemes other than bar-coding may be used. Different identification information (for example, identification information stored in an RFID embedded on the label) may be read by an RFID reader for each drug or for all the drugs at a batch. Further, the number issued in a label by these bar codes and RFID may be used for disposal management of drugs or the like (including blood transfusion pack).

Next, in the determination of step S22, if the reason of the abnormal drug inspection result is not the excessive amount (No in step S22), the MPU 31 determines that the determination reason of the abnormal drug inspection result is a mistaken drug preparation in which a drug code of a drug that is not to be included in the mixed injection is mistakenly read during the sorting process, and performs a mistaken drug preparation notification screen display process (step S24).

The mistaken drug preparation notification screen display process and the label issue process (step S24) will be described referring to FIGS. 23 to 26.

Figure 24:
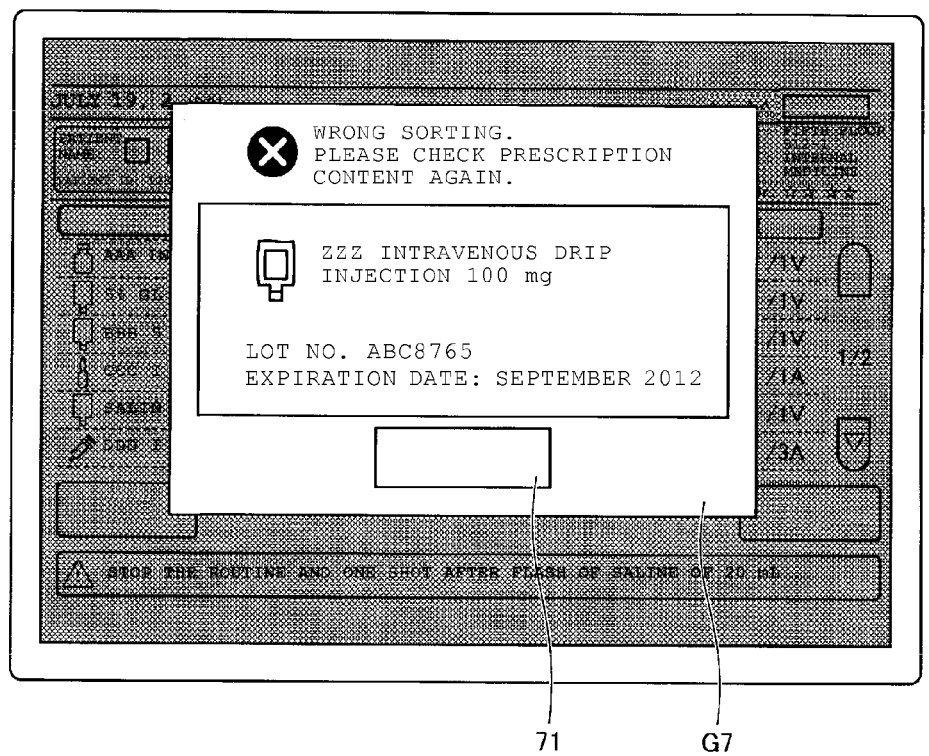
FIG. 24 is a diagram illustrating an example of a mistaken drug selection notification screen.
Figure 25:
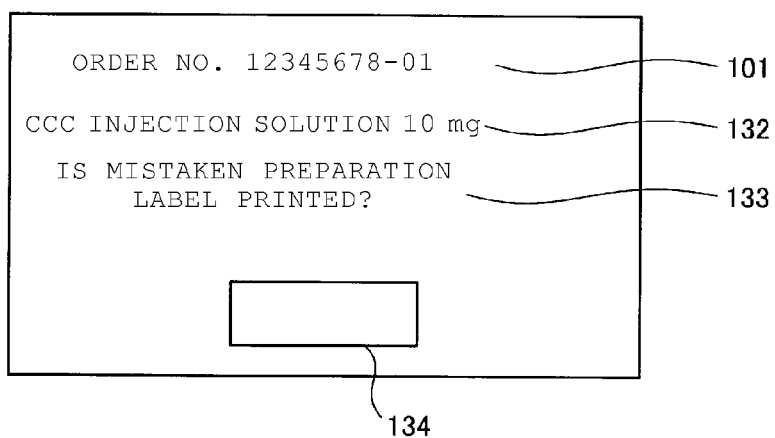
FIG. 25 is an example of a label issue screen when a drug is mistakenly prepared due to a mistaken drug selection.

As a result of the above-described drug inspection process (step S18), if it is determined that the drug is mistakenly prepared (No in step S22), a mistaken drug preparation notification screen G7 shown in FIG. 24 is displayed (step S101).

In FIG. 24, on the mistaken drug preparation notification screen G7, if there is a message "Wrong sorting. Please check prescription content again", and for example, a drug name of the drug that is mistakenly sorted is "ZZZ intravenous drip injection of 100 mg", the drug name "ZZZ intravenous drip injection of 100 mg", its lot number and expiration date are displayed. Further, on the mistaken drug preparation notification screen G7, the "close" button 71 is displayed.

If the operator confirms the content and taps the "close" button 71 displayed on the mistaken drug preparation notification screen G7, the MPU 31 determines whether the "close" button 71 is tapped (step S102). If it is determined that the "close" button 71 is tapped (Yes in step S102), the MPU 31 displays printing confirmation shown in FIG. 25 and displays a print button 134 (step S103). In the printing confirmation display, the order number 101, a drug name 132 of the drug that is inspected as being mistakenly prepared, and a confirmation message 133 on whether to print are displayed. The MPU 31 waits (No in step S104) until the print button 134 is tapped, and if the print button 134 is tapped (Yes in step S104), the MPU 31 transmits print data of the label to the printer 23 (step S105).

If the printer 23 receives the print data based on step S105, the printer 23 prints a label 137 shown in FIG. 26. On the label 137, the order number 101, a message 135 "mistaken drug preparation" that indicates that the drug is mistakenly prepared, information 136 about the drug, a bar code 138 that is obtained by coding and printing the order number 101, and individual information 139 such as a patient name, birth date, age and gender are printed.

The printer 23 issues the printed label 137 through the label issue port. In the vicinity of the label issue port, the sensor 23S detects the presence or absence of the label 137 according to whether the issued label 137 is removed. When the label 137 is not removed, the sensor 23S outputs a detection signal that indicates that the label 137 is present, and when the label 137 is removed, the sensor 23S outputs a detection signal that indicates that the label 137 is not present.

The MPU 31 determines whether the detection signal that indicates that the label 137 is removed and the label 137 is not present is output from the sensor 23S (step S106), and waits until it is determined that the signal is output (No in step S106). If it is determined that the signal is output (Yes in step S106), the screen display process when the inspection result shown in FIG. 10 is abnormal is executed, for example (step S25 in FIG. 4).

As described above, in the present exemplary embodiment, when the MPU 31 determines that the drug is mistakenly prepared, since the label 137 on which the message that represents that the drug is mistakenly prepared is printed is issued, it is possible to attach the label of the mistaken drug preparation to the drug at an optimal timing. Regardless of the present exemplary embodiment, it is preferable that a message that enables determining that the drug is mistakenly prepared be printed on the label 137.

Further, since the MPU 31 can be set to only to be able to execute the next process under the condition that it is determined that the label is removed and the label is not present, it is possible to prevent omission of the label attachment.

Since the bar code 138 obtained by coding the order number 101 is printed on the label 137, instead of displaying the inspection result screen under the condition that the signal of the sensor 23S is received, the inspection result screen may be displayed under the condition that the bar code 138 is read by the scanner 37 and the order number included in the read bar code 138 matches with the order number 101 of the drug mixed injection.

In the present exemplary embodiment, the order number 101 is coded as the bar code 138, but a different management number may be bar-coded. Coding schemes other than bar-coding may be used. Different identification information (for example, identification information stored in an RFID embedded on the label) may be read by an RFID reader for each drug or for all the drugs at a batch. Further, the number issued in a label by these bar codes and RFID may be used for disposal management of drugs or the like (including blood transfusion pack).

Here, the description will be made again referring to the display screen of the inspection result in FIG. 10.

In the case of the display screen G5 of the inspection result in FIG. 10, for example, if the read drug code is a drug name "CCC injection solution of 10 mg" and the expiration date expires, a mark M3 that represents that the inspection is abnormal, that is, there is the same drug of which the expiration date thereof expires ("mark X" in FIG. 10) at the time point shown in FIG. 7, instead of one mark M1 that represents that it is necessary to include one ampoule bottle in total is displayed in the instructed amount display area 63 of a section of a drug name "CCC injection solution of 10 mg" that is present in the fourth row from the top of the list. Further, for example, the section of the drug name "CCC injection solution of 10 mg" is changed into a red line display RL that represents that the drug corresponding to the corresponding section is abnormal in inspection.

As described above, if there is an abnormal inspection among the drugs displayed in the drug list, since the corresponding section enters a state indicating the abnormal inspection (in this case, the red line display RL), the operator is able to easily detect the abnormal inspection results.

Further, in the instructed amount display area 63, since only the marks of which the total number is already sorted is changed into different marks for display compared with the case before the sorting, the operator may easily recognize how many times the sorting should be performed.

Further, in this case, the abnormal inspection reason may be linked to the mark M3 to tap the mark M3, so that display of the corresponding reason (display corresponding to one of the displays in FIGS. 16, 20, and 24) may be performed.

In the determination of step S14, if the response of the electronic medical report server 11 or the pharmacy server 19 is not the transmission of the list data including the drugs to be included in the mixed injection corresponding to the order number, this means that there is an error in the order content (Yes in step S14), and thus, the MPU 31 determines whether the content of the error is an error that represents that the drug sorting has already been executed (step S26) that is, whether the prescription has already been filled.

In the determination of step S26, if the error content represents that the drug preparation is already executed (Yes in step S26), the MPU 31 performs an execution information confirming instruction screen display process (step S27).

Figure 27:
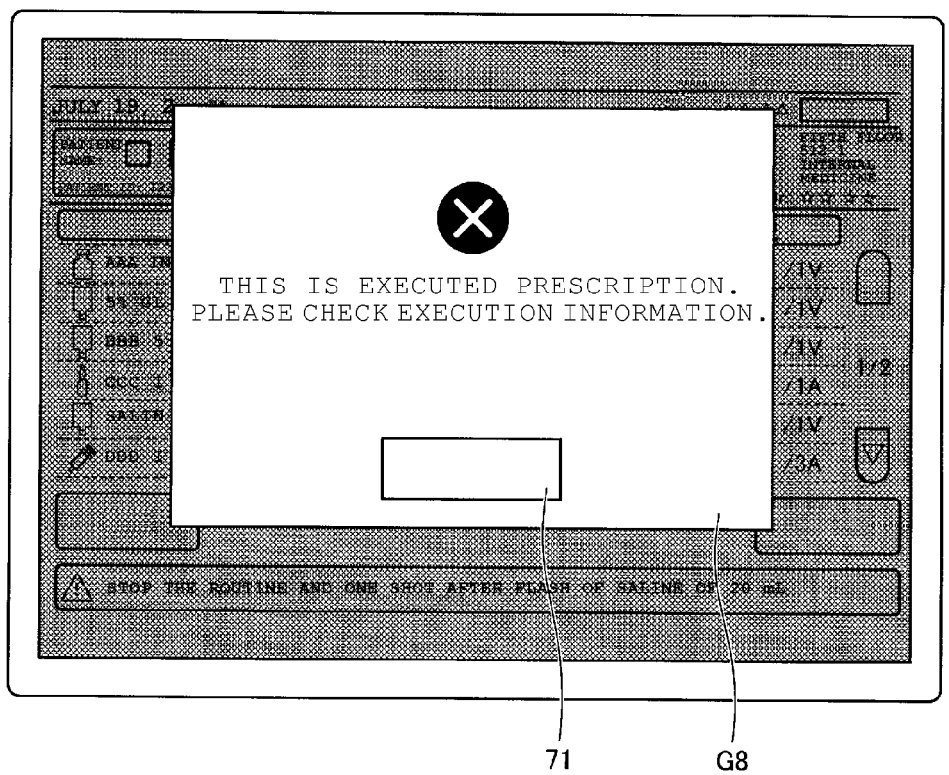
FIG. 27 is a diagram illustrating an example of an execution information confirmation instruction screen.

FIG. 27 is a diagram illustrating an example of an execution information confirming instruction screen.

On an execution information confirming instruction screen G8, a message "Executed prescription. Please check execution information." is displayed.

Then, if the operator checks the content and taps the "close" button 71 displayed on the execution information confirming instruction screen G8, the process proceeds to step S11. Then, the login screen G1 is displayed, and thereafter, the same processes are performed.

In the determination of step S26, if the error content represents that the mixed injection preparation is not already executed (No in step S26), the MPU 31 determines whether the error content represents an error that there has been a change in content of the prescription, that is, content of the order (step S28).

In the determination of step S28, if the error content represents that there is the change in the order content (Yes in step S28), the MPU 31 performs a medical record confirming instruction screen display process (step S29).

Figure 28:
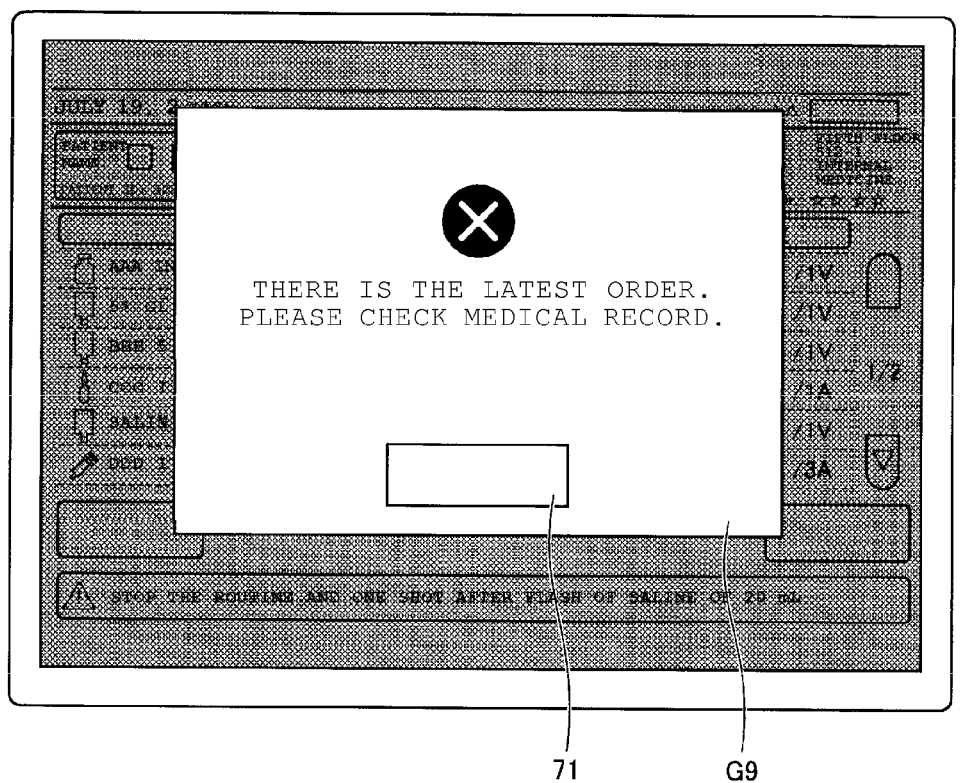
FIG. 28 is a diagram illustrating an example of a medical record update confirmation instruction screen.

FIG. 28 is a diagram illustrating an example of a medical record confirming instruction screen.

On a medical record confirming instruction screen G9, a message "This is the latest order. Please check medical record." is displayed.

Then, if the operator checks the content and then taps the "close" button 71 displayed on the medical record confirming instruction screen G9, the procedure proceeds to step S11. Then, the login screen G1 is displayed, and thereafter, the same processes are performed.

In the determination of step S28, if the error content represents that there has been no change in the order content (No in step S28), the error is an error of re-preparation after the initial drug preparation, and thus, the MPU 31 performs a re-preparation confirmation screen display process (step S30).

Figure 29:
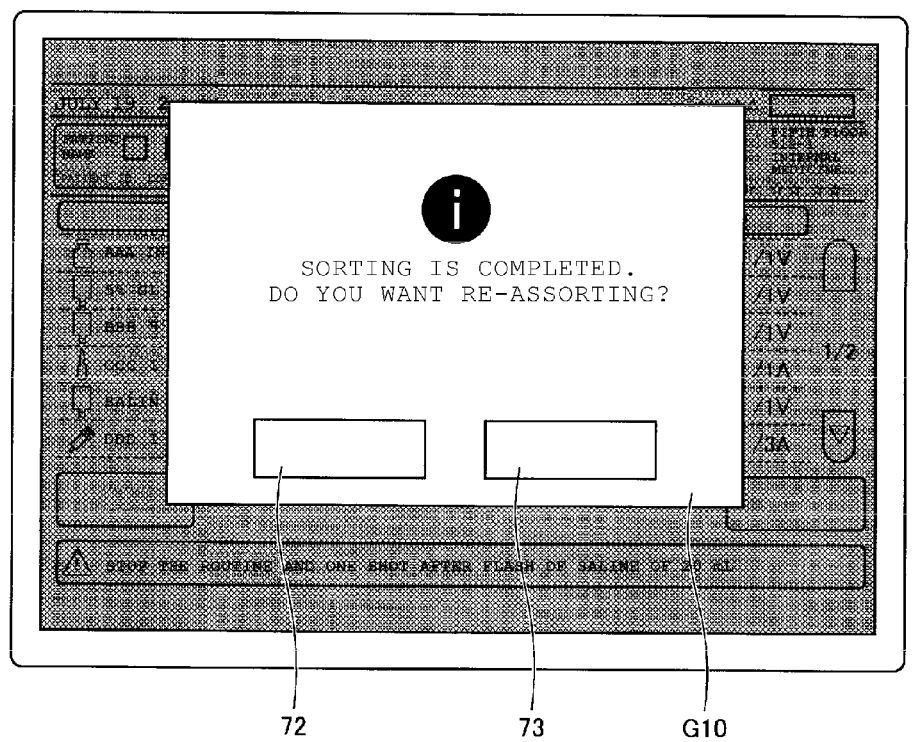
FIG. 29 is a diagram illustrating an example of a re-sorting confirmation screen.

FIG. 29 is a diagram illustrating an example of a re-preparation confirmation screen.

On a re-preparation confirmation screen G10, a message "Preparation is completed. Do you want re-preparation?" is displayed.

Further, on the re-preparation confirmation screen G10, a "Yes" button 72 tapped when the operator wants re-preparation and a "No" button 73 tapped when the operator does not want re-preparation are displayed.

Accordingly, the MPU 31 determines whether either the "Yes" button 72 or the "No" button 73 is tapped, that is, whether the operator wants re-preparation (step S31).

Figure 31:
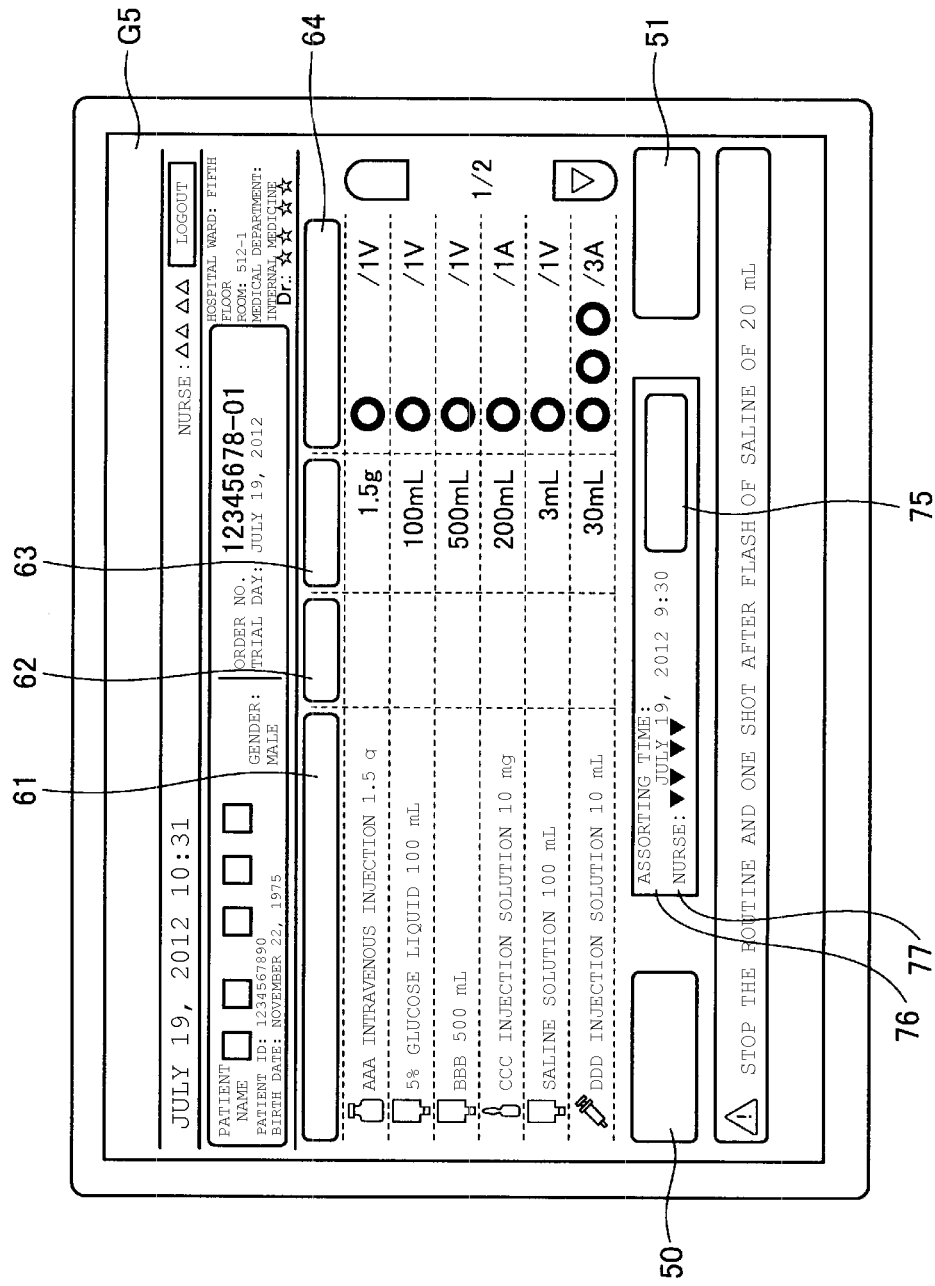
FIG. 31 is a diagram illustrating a display example of an order content display screen when re-sorting is desired.

FIG. 31 is a diagram illustrating a display example of an order content display screen when re-preparation is desired.

In the determination of step S31, if the operator taps the "Yes" button 72, that is, the operator wants re-preparation (Yes in step S31), a label 141 shown in FIG. 30 is issued from the printer 23 (step S32). The label 141 is a label attached to a drug returned for re-preparation, on which a mixed injection order number 142, a display 143 indicating that the drug is a returned drug, a message 144 indicating that the drug is being re-prepared, a returned drug name 145, a bar code 146 that is obtained by coding the order number 142, individual information 147 such as a patient name, birth date, gender, and the like are printed.

Further, under the condition that it is detected by the sensor 23S that the label 141 is removed and the label is not present, a re-preparation execution screen display process for displaying an order content display screen that is a re-preparation execution screen is performed (step S33), and the order content display screen is displayed (step S15).

Here, when the order content display screen G5 in FIG. 31 is displayed, since the preparation (drug inspection process) has already been completed once, a re-preparation button 75 is displayed in addition to the display screen of the inspection result when all the drugs shown in FIG. 11 are sorted. Further, the previous preparation time is displayed in a previous preparation time display area 76, and a name of a person responsible for the previous preparation (a name of a person responsible for the previous drug inspection) is displayed in a previous responsible person name display area 77.

Accordingly, as the operator taps the re-preparation button 75, the order content display screen G5 is displayed again in the initial state shown in FIG. 7, and thereafter, the same drug inspection process is performed.

Next, a button tapping process that is performed in association with the above process will be described.

Figure 32:
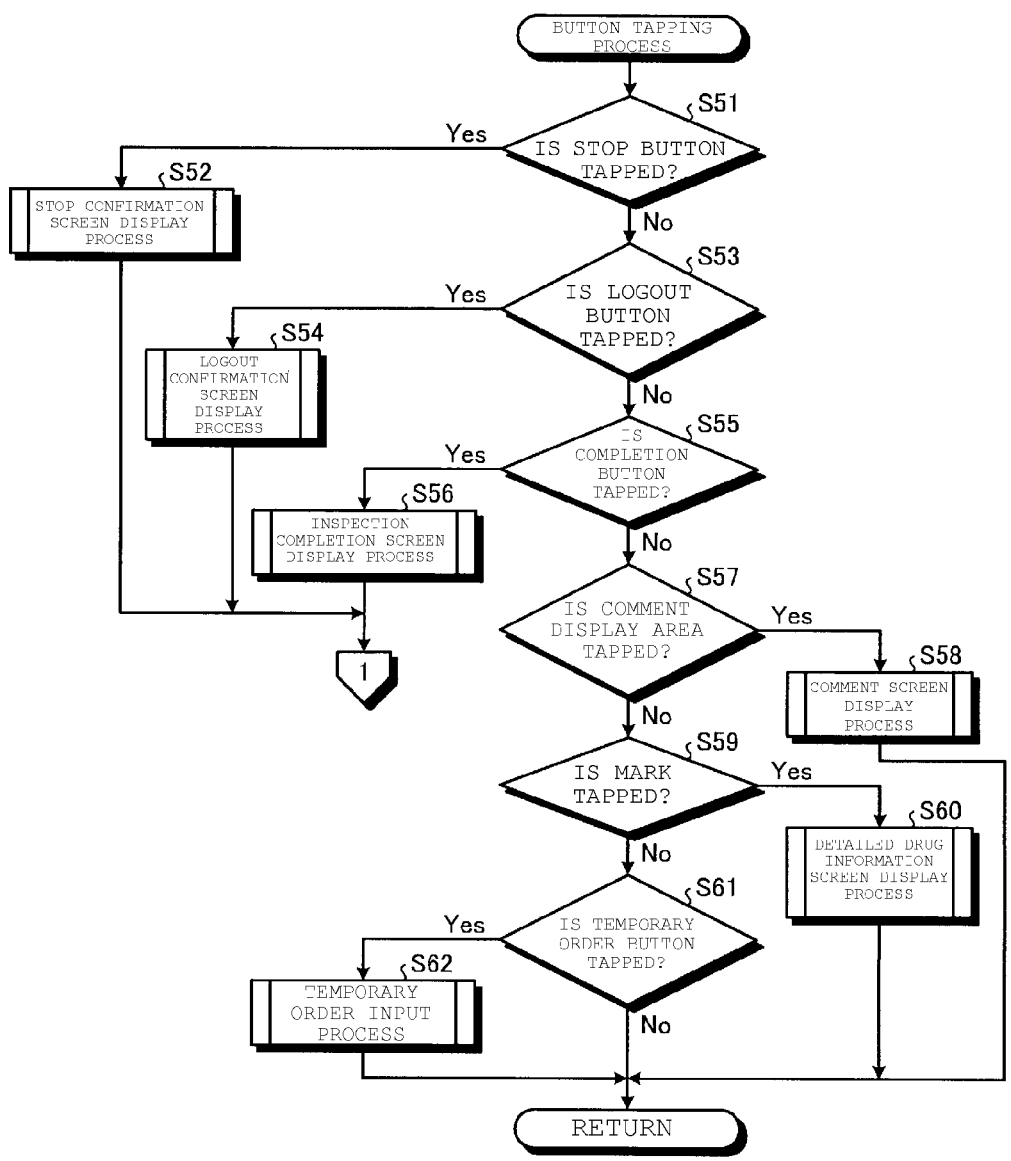
FIG. 32 is a flowchart of a button tapping process performed as an interruption process.

FIG. 32 is a processing flowchart of a button tapping process performed as an interruption process.

The MPU 31 in this embodiment inspects (monitors) button tapping at all times. If the button tapping is performed, first, the MPU 31 determines whether the stop button 50 shown in FIG. 7 is tapped (step S51).

In the determination of step S51, if the stop button 50 is tapped (Yes in step S51), the MPU 31 performs a stop confirmation screen display process (step S52).

Figure 33:
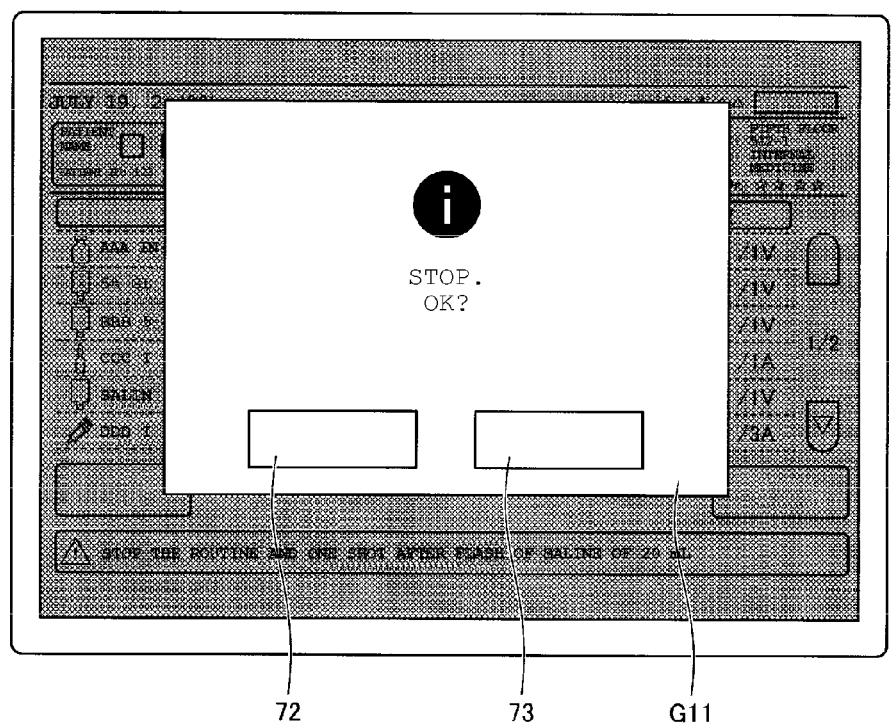
FIG. 33 is a diagram illustrating an example of a stop confirmation screen.

FIG. 33 is a diagram illustrating an example of a stop confirmation screen.

On a stop confirmation screen G11, a message "Stop. OK?" is displayed.

Further, on the stop confirmation screen G11, a "Yes" button 72 tapped when the operator wants to stop the drug inspection process and a "No" button 73 tapped when the operator does not want to stop the drug inspection process are displayed.

Accordingly, if the "Yes" button 72 is tapped, that is, if the operator wants to stop the drug inspection process, the procedure proceeds to step S11, and the MPU 31 displays the login screen G1 again to enter a standby state.

On the other hand, if the "No" button 73 is tapped, the MPU 31 returns to the display screen in which the stop button 50 is tapped, and then continues the subsequent processes.

In the determination of step S51, if the stop button 50 is not tapped (No in step S51), the MPU 31 determines whether the logout button 43 shown in FIG. 7 is tapped (step S53).

In the determination of step S53, if the logout button 43 is tapped (Yes in step S53), the MPU 31 performs a logout confirmation screen display process (step S54).

Figure 34:
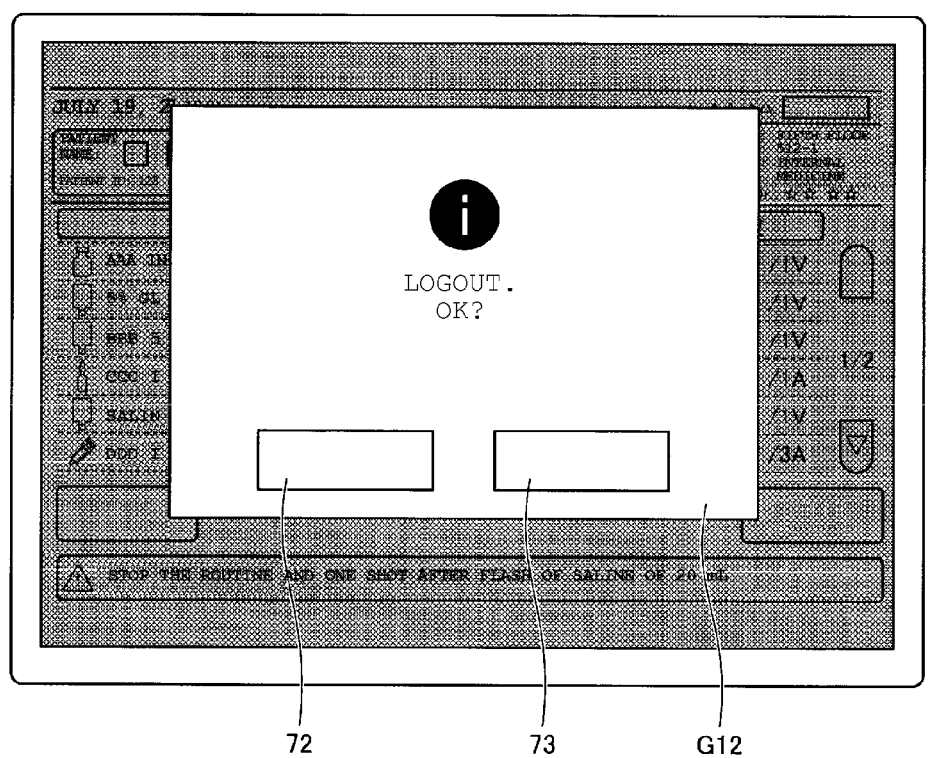
FIG. 34 is a diagram illustrating an example of a logout confirmation screen.

FIG. 34 is a diagram illustrating an example of a logout confirmation screen.

On a logout confirmation screen G12, a message "Logout. OK?" is displayed.

Further, on the logout confirmation screen G12, a "Yes" button 72 tapped when the operator wants logout and a "No" button 73 tapped when the operator does not want logout are displayed.

Accordingly, if the "Yes" button 72 is tapped, that is, if the operator wants logout, the procedure proceeds to step S11, and the MPU 31 displays the login screen G1 again to enter a standby state.

On the other hand, if the "No" button 73 is tapped, the MPU 31 returns to the display screen in which the logout button 43 is tapped, and then continues the subsequent processes.

In the determination of step S53, if the logout button 43 is not tapped (No in step S53), the MPU 31 determines whether the completion button 51 shown in FIG. 11 is tapped (step S55).

In the determination of step S55, if the completion button 51 is tapped (Yes in step S55), the MPU 31 performs an inspection completion screen display process in which the inspection completion screen shown in FIG. 9 is displayed (step S56). Then, the procedure proceeds to step S11, and then, the MPU 31 displays the login screen G1 again to enter a standby state.

In the determination of step S55, if the completion button 51 is not tapped (No in step S55), the MPU 31 determines whether the comment display area 52 shown in FIG. 7 is tapped (step S57).

In the determination of step S57, if the comment display area 52 shown in FIG. 7 is tapped (Yes in step S57), the MPU 31 performs a comment screen display process (step S58).

Figure 35:
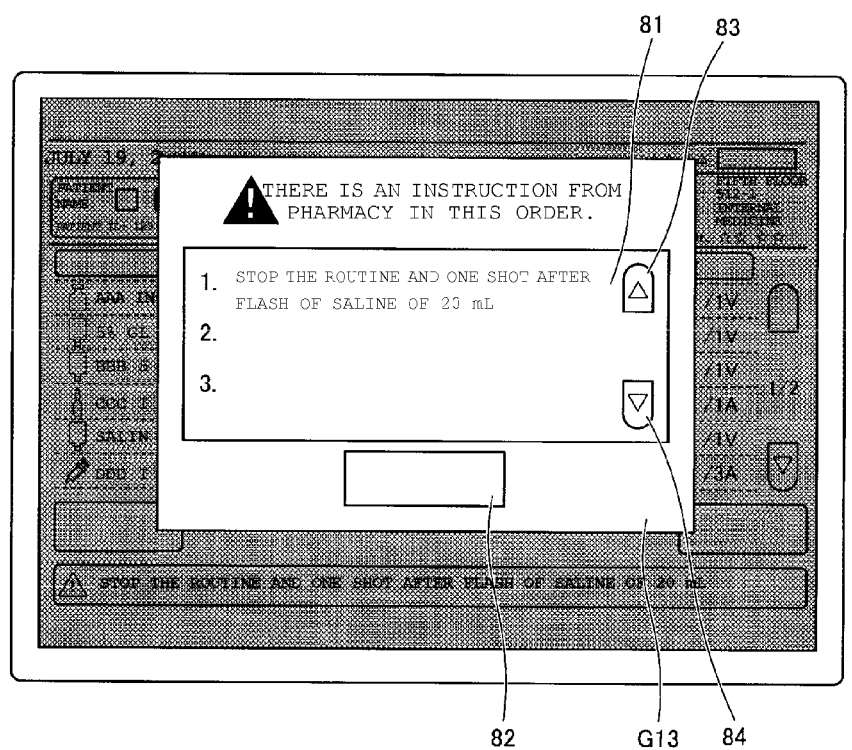
FIG. 35 is a diagram illustrating an example of a comment screen.

FIG. 35 is a diagram illustrating an example of a comment screen.

A comment screen G13 is a screen on which an instruction comment from a pharmacy in a corresponding prescription is displayed.

On the comment screen G13, a message "There is an instruction from the pharmacy in this order" is displayed.

Further, a comment display 81 that displays the instruction from the pharmacy, a "close" button 82 for closing the comment screen G13, an up-scroll button 83 for scrolling the comment upward, and a down-scroll button 84 for scrolling the comment downward are displayed on the comment screen G13.

Accordingly, if the up-scroll button 83 or the down-scroll button 84 is tapped, the MPU 31 enables the comment to be scrolled upward or downward in the comment display 81.

Further, if the "close" button 82 is tapped, the MPU 31 returns to the display screen on which the comment display area 52 is tapped, and then continues the subsequent processes.

In the determination of step S57, if the comment display area 52 is not tapped (No in step S57), the MPU 31 determines whether the mark M2 corresponding to the drug of which the drug inspection shown in FIG. 10 is normally terminated is tapped (step S59).

In the determination of step S59, if the mark M2 corresponding to the drug of which the drug inspection shown in FIG. 10 is normally terminated is tapped (Yes in step S59), the MPU 31 performs a detailed drug information screen display process of displaying detailed information about the drug corresponding to the mark M2 (step S60).

Figure 36:
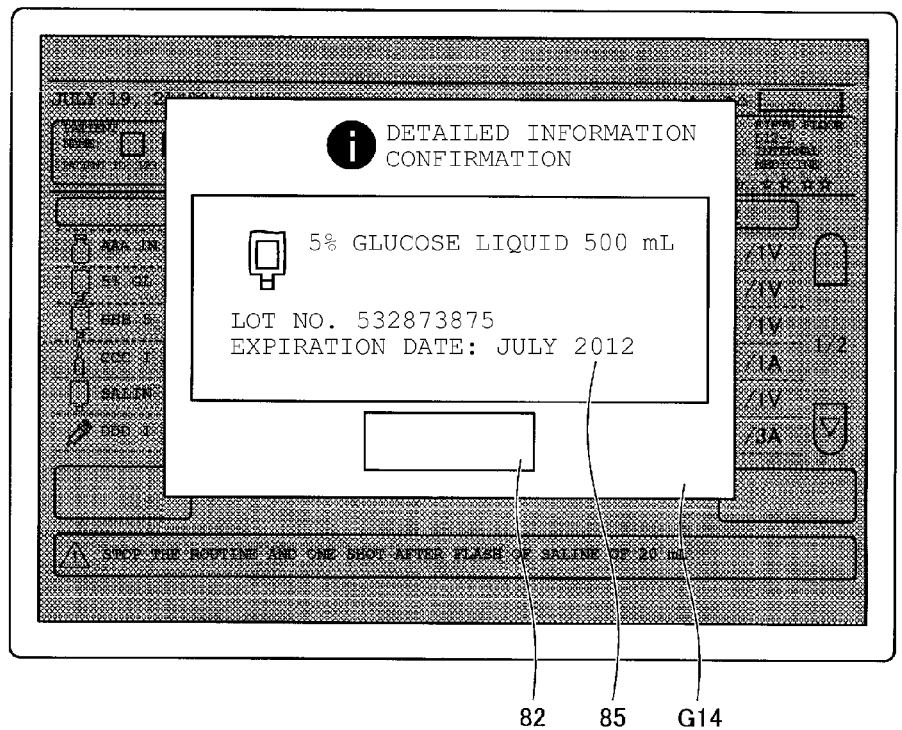
FIG. 36 is a diagram illustrating an example of a detailed drug information screen.

FIG. 36 is a diagram illustrating an example of a detailed drug information screen.

On a detailed drug information screen G14, a message "Detailed information confirmation" is displayed.

Further, on the detailed drug information screen G14, a detailed information display unit 85 that displays a drug name (in the case of an example in FIG. 36, "5% glucose liquid of 500 mL"), a lot number and an expiration date, and a "close" button 82 for closing the detailed drug information screen G14 are displayed as a detailed drug information corresponding to the mark M2.

Accordingly, if the "close" button 82 is tapped, the MPU 31 returns to the display screen in which the mark M2 is tapped, and then continues the subsequent processes.

In the determination of step S59, if the mark M2 corresponding to the drug of which the drug inspection is normally terminated is not tapped (No in step S59), the MPU 31 determines whether the temporary order button B1 shown in FIG. 6 is tapped (step S61).

In the determination of step S61, if the temporary order button B1 shown in FIG. 6 is tapped (Yes in step S61), the MPU 31 performs a temporary order input process (step S62).

Figure 37:
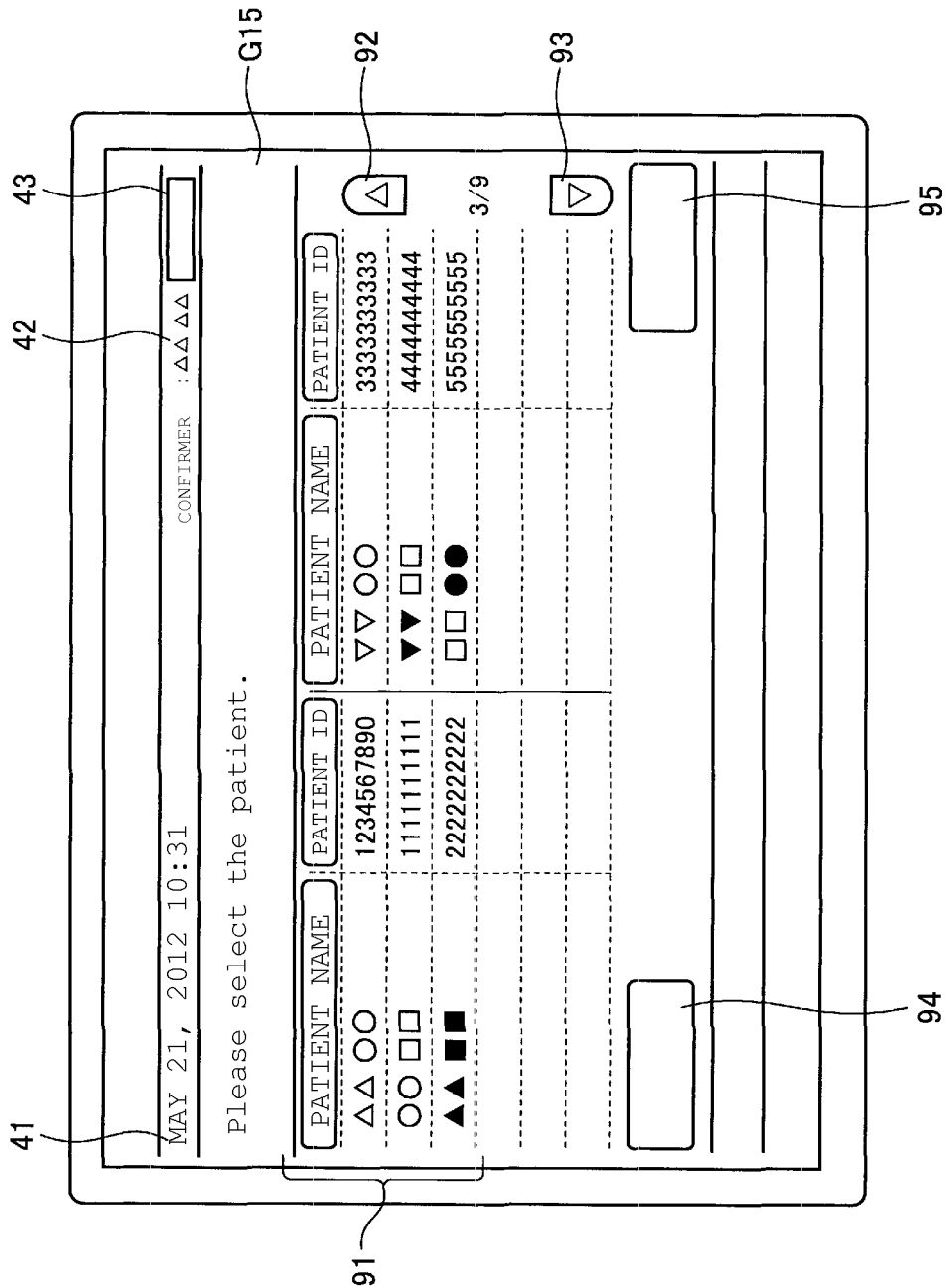
FIG. 37 is a diagram illustrating an example of an initial screen of a temporary order input process.

FIG. 37 is a diagram illustrating an example of an initial screen of the temporary order input process.

On an initial screen G15 of the temporary order input process, a message "Please select the patient." is displayed.

Further, on the initial screen G15 of the temporary order input process, a patient list display selection area 91 in which a list of patient names that are input targets of a temporary order is displayed in a selectable manner, an up-scroll button 92 for scrolling the patient list upward in the patient list display selection area 91, a down-scroll button 93 for scrolling the patient list downward in the patient list display selection area 91, a button 94 for returning to the order number input screen G2 shown in FIG. 6, and a select button 95 for selecting any patient selected in the patient list display selection area 91 are displayed.

Accordingly, if selection of any patient is made by the select button 95, the MPU 31 proceeds to the temporary order input process with respect to the corresponding patient.

According to the present exemplary embodiment, the amount of a drug to be actually included in the mixed injection or the like is improved. A method of using the scale 25 for prevention of prescription errors will be described here.

The MPU 31 records measured weights of each drug before and after an actual mixed injection preparation, using the scale 25 to obtain the measured weights. Further, the MPU 31 records a weight difference before and after the mixed injection work in the external storage unit 34 in correspondence with the drug identification.

This is because when the drug is accommodated in a vial, for example, when a mixed injection preparation is performed, the vial may not be entirely used or a part of the vial may be consumed by an injector preparation (such a syringe flush) or the like. Consequently, if the weight difference before and after the use of the drug is calculated, it is possible to detect the amount of the drug used in the actual mixed injection work.

Further, the MPU 31 compares the amount of the drug used in the actual mixed injection work with the instructed amount shown in the instruction data (the amount displayed in the instructed amount display area 63), and if the difference is within an allowable difference range, the MPU 31 determines that the mixed injection preparation is correctly performed. In this case, if the instructed amount is designated as a capacity, the weight difference is converted into the capacity by the MPU 31.

On the other hand, if the difference between the amount of the drug used in the actual mixed injection work and the instructed amount shown in the instruction data exceeds the allowable difference, the MPU 31 notifies that the mixed injection work is not correctly performed.

Consequently, the mixed injection terminal 14 inspects the mixed injection preparation, to thereby make it possible to prevent the prescription from being administered to a patient in a preparation error state.

The control program executed in the drug mixed injection preparation managing apparatus of the present exemplary embodiment is recorded for provision on a computer-readable recording medium such as a CD-ROM, a flexible disk (FD), a CD-R or a digital versatile disk (DVD) as a file of an installable format or an executable format.

Further, the control program executed in the drug mixing preparation managing apparatus of the present exemplary embodiment may be stored in a computer connected to a network such as the Internet and may be downloaded through the network for provision. Further, the control program executed in the drug mixing preparation managing apparatus of the present exemplary embodiment may be provided or distributed through the network such as the Internet.

Further, the control program executed in the drug mixing preparation managing apparatus of the present exemplary embodiment may be provided by being installed in a ROM or the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of managing a mixed injection preparation process, comprising:
   obtaining a mixed injection preparation instruction;
   obtaining information about a candidate drug for inclusion in a mixed injection in accordance with the mixed injection preparation instruction;
   comparing the information about the candidate drug to the mixed injection preparation instruction;
   determining whether the mixed injection is prepared in accordance with the mixed injection preparation instruction based on the information about the candidate drug;
   printing a label with a printer, the label indicating that the mixed injection is prepared in accordance with the mixed injection preparation instruction; and
   determining whether the label is removed from the printer.

2. The method of claim 1, wherein information about the candidate drug is obtained using a barcode reader.

3. The method of claim 1, wherein information about the candidate drug is obtained using a radio frequency identification tag.

4. The method of claim 1, wherein an optical sensor is used for determining whether the label has been removed from the printer.

5. The method of claim 1, wherein whether the label is removed from the printer is determined by reading an identification code printed on the label with a reader.

6. The method of claim 1, wherein the information about the candidate drug includes a weight of the candidate drug before the mixed injection is prepared and a weight of the candidate drug after the mixed injection is prepared.

7. The method of claim 1, wherein the mixed injection preparation instruction is obtained from a medical records server.

8. The method of claim 1, wherein the information about the candidate drug is obtained by reading a barcode on a container of the candidate drug.

9. A drug mixing preparation managing apparatus comprising:
   a printer configured to print labels;
   a reader configured to read identification information;
   a communication interface configured to obtain information based on identification information read by the reader;
   a drug inspection module configured to compare information about a candidate drug for inclusion in a mixed injection with a mixed injection preparation instruction and to determine whether the mixed injection is prepared in accordance with the mixed injection preparation instruction; and
   a label issue module configured to cause the printer to print a label to be directly or indirectly attached to the mixed injection after the drug inspection module determines whether the mixed injection is prepared in accordance with the mixed injection preparation instruction, the label issue module configured to detect whether the label is removed from the printer.

10. The drug mixing preparation managing apparatus according to claim 9, wherein when the mixed injection is determined by the drug inspection module to be prepared in accordance with the mixed injection preparation instruction, the label issue module causes the printer to print a label indicating that the mixed injection has been prepared in accordance with the mixed injection preparation instruction.

11. The drug mixing preparation managing apparatus according to claim 9, wherein the information about the candidate drug that is compared to the mixed injection preparation instruction by the drug inspection module includes at least one of an expiration date of the candidate drug, a name of the candidate drug, and a dosage level of the candidate drug.

12. The drug mixing preparation managing apparatus according to claim 11, further comprising a scale for measuring the dosage level of the candidate drug.

13. The drug mixing preparation managing apparatus according to claim 9, wherein the drug inspection module is configured to execute the next drug inspection process when the label has been removed from the printer and to not execute the next drug inspection process when the label has not been removed from the printer.

14. The drug mixing preparation managing apparatus according to claim 9, wherein an optical sensor is used to detect whether the label has been removed from the printer.

15. The drug mixing preparation managing apparatus according to claim 9, wherein label issue module detects whether the label is removed by determining whether identification information printed on the label is read by the reader.

16. The drug mixing preparation managing apparatus according to claim 9, further comprising a touch panel display unit for displaying information based on identification information read by the reader.

17. The drug mixing preparation managing apparatus according to claim 9, wherein the reader is a barcode reader.

18. The drug mixing preparation managing apparatus according to claim 9, further comprising:
- a scale to obtain a weight of the candidate drug before the mixed injection is prepared and a weight of the candidate drug after the mixed injection is prepared;
- a touch panel display unit configured to display information based on identification information read by the reader; and
- a camera configured to acquire images of an operator of the drug mixing preparation managing apparatus.

19. A non-transitory, computer-readable medium storing program instructions for a drug mixing preparation apparatus that when executed cause the apparatus to perform steps of:

obtaining a mixed injection preparation instruction;

obtaining information about a candidate drug for inclusion in a mixed injection in accordance with the mixed injection preparation instruction;

comparing the information about the candidate drug to the mixed injection preparation instruction;

determining whether the mixed injection is prepared in accordance with the mixed injection preparation instruction based on the information about the candidate drug;

printing a label using a printer, the label indicating whether the mixed injection has been prepared in accordance with the mixed injection preparation instruction; and determining whether the label is removed from the printer.

20. The non-transitory, computer-readable medium of claim 19, wherein the mixed injection preparation instruction is obtained from a medical records server.

* * * * *